(12) United States Patent
Berglund et al.

(10) Patent No.: US 9,751,918 B2
(45) Date of Patent: Sep. 5, 2017

(54) TRANSGENIC PLANTS EXPRESSING COBALAMIN BINDING PROTEINS

(75) Inventors: Lars Erik Berglund, Odder (DK); Torben Ellebaek Petersen, Skanderborg (DK); Sergey Nikolaevich Fedosov, Abyhoj (DK); Ebba Nexo, Abyhoj (DK); Niels Bech Laursen, Hojbjerg (DK); Erik Ostergaard Jensen, Abyhoj (DK)

(73) Assignee: XERAGENX LLC, St. Louis, MO (US)

( * ) Notice: Subject to any disclaimer, the term of this patent is extended or adjusted under 35 U.S.C. 154(b) by 863 days.

(21) Appl. No.: 12/357,622

(22) Filed: Jan. 22, 2009

(65) Prior Publication Data
US 2010/0184642 A1    Jul. 22, 2010

Related U.S. Application Data

(63) Continuation of application No. 10/483,849, filed as application No. PCT/GB02/03227 on Jul. 12, 2002, now abandoned.

(30) Foreign Application Priority Data

Jul. 13, 2001 (GB) .................................. 0117171.9

(51) Int. Cl.
| | |
|---|---|
| C07K 14/47 | (2006.01) |
| C12N 15/82 | (2006.01) |
| A61K 31/7056 | (2006.01) |
| A61K 38/16 | (2006.01) |
| A61K 47/48 | (2006.01) |
| C07K 14/415 | (2006.01) |
| C12N 5/071 | (2010.01) |
| A61K 38/00 | (2006.01) |

(52) U.S. Cl.
CPC .......... *C07K 14/47* (2013.01); *A61K 31/7056* (2013.01); *A61K 38/168* (2013.01); *A61K 47/48107* (2013.01); *C07K 14/415* (2013.01); *C12N 5/0602* (2013.01); *C12N 15/8257* (2013.01); *A61K 38/00* (2013.01); *C12N 2500/38* (2013.01)

(58) Field of Classification Search
None
See application file for complete search history.

(56) References Cited

U.S. PATENT DOCUMENTS

| | | | |
|---|---|---|---|
| 4,279,886 A | * | 7/1981 | Allen .......................... 424/1.53 |
| 5,869,466 A | * | 2/1999 | Russell-Jones et al. ........ 514/52 |
| 5,939,288 A | | 8/1999 | Thornburg |
| 5,959,187 A | | 9/1999 | Bailey et al. |
| 7,741,539 B2 | * | 6/2010 | Gorr .................... C12N 9/1048 435/419 |
| 8,907,163 B2 | * | 12/2014 | Bakker ................ C12N 9/1051 435/419 |

FOREIGN PATENT DOCUMENTS

| | | |
|---|---|---|
| SU | 1751207 | 7/1992 |
| WO | PCT/US02/04909 A2 | 8/2002 |

OTHER PUBLICATIONS

Rishi et al (2001 Journal of Plant Biochemistry and Biotechnology 1:1-12. Published Jan. 2001.*
Allen, Robert H., M.D. (1975) Human Vitamin B-12 Transport Proteins, Progress in Hematology 9, pp. 57-84.
Aminoff, et al., (1999) Nature Genetics, 21:309-313.
Chrispeels, et al., (1996) The Production of Recombinant Glycoproteins With Defined Non-Immunogenic Glycans in Transgenic Plants: A Production System for Industrial and Pharmaceutical Proteins; Editors: Owen and Pen, pp. 99-113.
Clough, Steven J., et al. (1998) Floral Dip: A Simplified Method for Agrobacterium-Mediated Transformation of Arabidopsis Thaliana, The Plant Journal 16(6), pp. 735-743.
Dieckgraefe, B. K., et al., (Jan. 1988) Isolation and Structural Characterization of a cDNA Clone Encoding Rate Gastric Instrinsic Factor, Proc. Natl. Acad. Sci. USA, vol. 85, Jan. 1988, pp. 46-50.
Fedosov, Sergey N., et al., (1999) Sequence, S-S Bridges, and Spectra of Bovine Transcobalamin Expressed in Pichia Pastoris, The Journal of Biological Chemistry, vol. 274, No. 37, Issue of Sep. 10, pp. 26015-26020.
Fischer, et al., (2000) Transgenic Research 9:279-299.
Fowler, (Apr. 1998) Genetic Defects of Folate and Cobalamin Metabolism, Eur J Pediatr. 157 Suppl 2:S60-6.
Giddings, Glynis, et al., (Nov. 2000) Transgenic Plants as Factories for Biopharmaceuticals, Nature Biotechnology, vol. 18, pp. 1151-1155.
Gordon, M., et al., (1992) In Vitro Expression and Secretion of Functional Mammalian Intrinsic Factor Using Recombinant Baculovirus, Biochimica et Biophysica Acta., 1132 (1992), pp. 276-283.
Gordon, Marilyn M., et al., Expression of Functional Intrinsic Factor Using Recombinant Baculovirus Methods in Enzymology, vol. 281, pp. 255-261.
Hall, C. A., et al., (1977) Congenital Deficiency of Human R-Type Binding Proteins of Cobalamin, American Society of Human Genetics, pp. 619-626.
Hewitt, J. E., et al., (Feb. 1991) Human Gastric Intrinsic Factor: Characterization of cDNA and Genomic Clones and Localisation to Human Chromosome 11, Genomics, pp. 432-440.
Hideo, Niwa, et al., DNA Sequence Encoding Human Intrinsic Factor, JP5015375.

(Continued)

*Primary Examiner* — Brent Page

(57) ABSTRACT

The present invention relates to the use of transgenic plants for the expression of vitamin B12 (cobalamin) binding proteins. Plant cells are transformed with nucleotide sequences adapted for expression and secretion of vitamin B12 binding proteins. The present invention also relates to the use of recombinant vitamin B12 binding proteins from plants in analytical tests and treatment of vitamin B12 deficiency. Also disclosed is a method for purification of recombinant vitamin B12 binding proteins.

1 Claim, 9 Drawing Sheets

(56) References Cited

OTHER PUBLICATIONS

Figure 8:
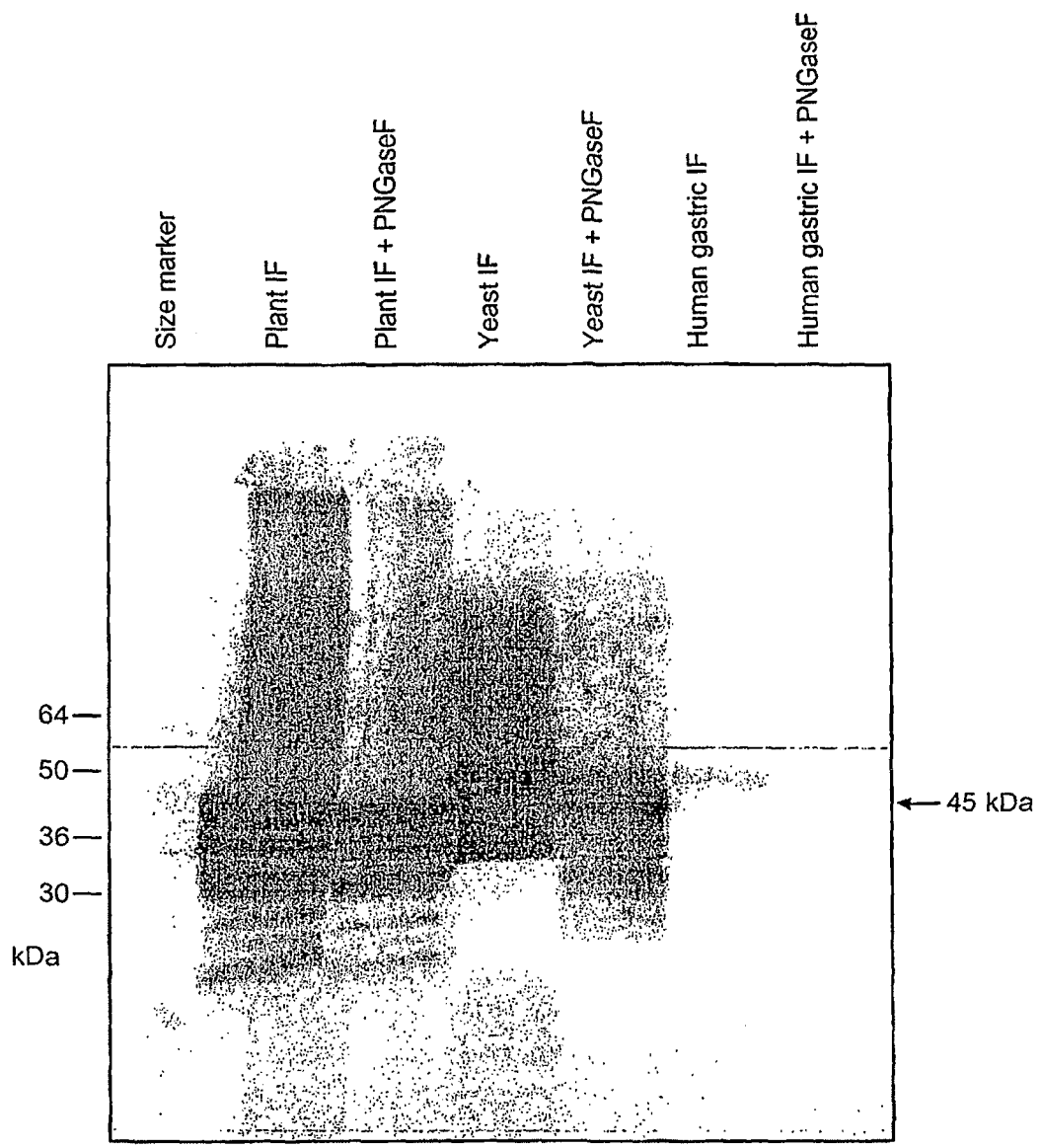

Hvas, et al., (Jun. 2005) Recombinant Human Intrinsic Factor Increases the Vitamin B-12 Absorption Among Individuals With Obvious Biochemical . . . Haematologica Reports 1:3: 13.

Johnston, J., et al., (Sep. 1989) Structure of the cDNA Encoding Transcobalamin I, a Neutrophil Granule Protein, The Journal of Biological Chemistry, vol. 264, No. 27, pp. 15754-15757.

Katz, Max, et al., (May 1974) Isolation and Characterization of an Abnormal Human Intrinsic Factor, The Journal of Clinical Investigation, vol. 53, pp. 1274-1283.

Koncz, Csaba, et al., (1986) The Promoter of T2—DNA Gene 5 Controls the Tissue-Specific Expression of Chimaeric Genes Carried by a Novel Type of Agrobacterium Binary Vector, Mol. Gen. Genet 204, pp. 383-396.

Li, Ning, et al., (1994) Identification of Two Mutant Alleles of Transcobalamin II in an Affected Family, Oxford University Press, Human Molecular Genetics, vol. 3, No. 10, pp. 1835-1840.

Ma, Julian K-C., et al., (Oct. 2003) The Production of Recombinant Pharmaceutical Proteins in Plants, Nature Reviews Genetics, vol. 4, pp. 793-805.

Magnuson, Nancy S., et al., (1998) Secretion of Biologically Human Interleukin-2 and Interleukin-4 from Genetically Modified Tobacco Cells in Suspension Culture, Protein Expression and Purification, vol. 13., pp. 45-52.

Nexo, Ebba, (1998) Cobalamin Binding Proteins, Department of Clinical Biochemistry, KH, Aarhus University Hospital, pp. 461-475.

Nexo, Ebba, et al., (1975) A New Principle in Biospecific Affinity Chromatography Used for Purification of Cobalamin-Binding Proteins, Biochimica et Biophysica Acta, 379, pp. 189-192.

Nexo, Ebba et al., (1981) Insolubilized Pure Human Intrinsic Factor Used for Quantitation of Cobalamins in Serum, Scand. J. clin. Lab. Invest. 41, pp. 465-468.

Nexo, Ebba, et al., (2000) Measurement of Transcobalamin by ELISA, Clinical Chemistry 46 (10), pp. 1643-1649.

Nexo, Ebba, et al., (1977) Unsaturated and Cobalamin Saturated Transcobalamin I and II in Normal Human Plasma, Scand. J. clin. Lab. Invest. 37 (1977), pp. 723-728.

Nicolas, Jean-Pierre, et al., (Sep. 1995) Gastric Intrinsic Factor and its Receptor, Bailliere's Clinical Haematology, vol. i, No. 3, pp. 515-531.

Niwa, et al., GenBank Accession E04240 in Sequence Alignment.

Quadros, Edward V., et al., (Mar. 1, 1993) Functional Human Transcobalamin II Isoproteins Are Secreted by Insect Cells Using the Baculovirus Expression System, Blood, vol. 81, No. 5, pp. 1239-1245.

Quadros, Edward V., et al., (1986) Purification and Molecular Characterization of Human Transcobalamin II, The Journal of Biological Chemistry, vol. 261, No. 33, pp. 15455-15460.

Rothenberg, Sheldon P., et al., (Sep. 1995) Transcobalamin II and the Membrane Receptor for the Transcobalamin II—Cobalamin Complex, Bailliere's Clinical Haematology, vol. 8, No. 3, pp. 499-514.

Seetharam, et al., (Oct. 1999) Cellular Import of Cobalamin (Vitamin B-12) J. Nutr. 129(10): 1761-4.

Stupperich, Erhard, et al., (1991) Effect of the Cobalt-N Coordination on the Cobamide Recognition by the Human Vitamin B-12 Binding Proteins Intrinsic Factor, Transcobalamin and Haptocorrin, Eur. J. Biochem., 199, pp. 299-303.

Van Kapel, J., et al., (1981) An Improved Method for Large Scale Purification of Human Holo-Transcobalamin II, BIochemica et Biophysica Acta, 676, pp. 307-313.

Wen, et al., (2000) Biochimica et Biophysica Acta 1490:43-53.

Wen, J., et al., (2000) Functional Expression in Pichia Pastoris of Human and Rat Intrinsic Factor, Biochimica et Biophysica ACTA, vol. 1490, pp. 43-53.

Wen, Jipu, (2000) Functional Expression in Pichia Pastoris of Human and Rat Intrinsic Factor, Biochimica et Biophysica Acta 1490, pp. 43-53.

Yamashita, Kenji, et al., DNA Sequence Coding Human Intrinsic Factor, JP5049478.

Alan, Isolation of Gastric Vitamin B12-binding Proteins Using Affinity Chromatography, The Journal of Biological Chemistry, May 25, 1973, pp. 3660-3669, vol. 248, No. 10.

Katz, Isoloation and Characterization of an Abnormal Human Intrinsic Factor, The Journal of Clinical Investigation, May 1974, pp. 1274-1283, vol. 53.

* cited by examiner

TCTAGAACTCACAACCTAGCTAGCTAGTAAACAGTATTTTCTATATACCA 50
AAAATGGCTTCAAGTTCCATAGCTCTTTTCTTGGCTCTCAATCTTCTCTT 100
TTTCACAACAATCTCCGCCAGTACCCAGACCCAGAGTTCATGCTCCGTTC 150
CCTCAGCACAGGAGCCCTTGGTCAATGGAATACAAGTACTCATGGAGAAC 200
TCGGTGACTTCATCAGCCTACCCAAACCCCAGCATCCTGATTGCCATGAA 250
TCTGGCCGGAGCCTACAACTTGAAGGCCCAGAAGCTCCTGACTTACCAGC 300
TCATGTCCAGCGACAACAACGATCTAACCATTGGGCAGCTCGGCCTCACC 350
ATCATGGCCCTCACCTCCTCCTGCCGAGACCCTGGGGATAAAGTATCCAT 400
TCTACAAAGACAAATGGAGAACTGGGCACCTTCCAGCCCCAACGCTGAAG 450
CATCAGCCTTCTATGGGCCCAGTCTAGCGATCTTGGCACTGTGCCAGAAG 500
AACTCTGAGGCGACCTTGCCGATAGCCGTCCGCTTTGCCAAGACCCTGCT 550
GGCCAACTCCTCTCCCTTCAATGTAGACACAGGAGCAATGGCAACCTTGG 600
CTCTGACCTGTATGTACAACAAGATCCCTGTAGGTTCAGAGGAAGGTTAC 650
AGATCCCTGTTTGGTCAGGTACTAAAGGATATTGTGGAGAAAATCAGCAT 700
GAAGATCAAAGATAATGGCATCATTGGAGACATCTACAGTACTGGCCTCG 750
CCATGCAGGCTCTCTCTGTAACACCTGAGCCATCTAAAAAGGAATGGAAC 800
TGCAAGAAGACTACGGATATGATACTCAATGAGATTAAGCAGGGGAAATT 850
CCACAACCCCATGTCCATTGCTCAAATCCTCCCTTCCCTGAAAGGCAAGA 900
CATACCTAGATGTGCCCCAGGTCACTTGTAGTCCTGATCATGAGGTACAA 950
CCAACTCTACCCAGCAACCCTGGCCCTGGCCCCACCTCTGCATCTAACAT 1000
CACTGTCATATACACCATAAATAACCAGCTGAGGGGGGTTGAGCTGCTCT 1050
TCAACGAGACCATCAATGTTAGTGTGAAAAGTGGGTCAGTGTTACTTGTT 1100
GTCCTAGAGGAAGCACAGCGCAAAAATCCTATGTTCAAATTTGAAACCAC 1150
AATGACATCTTGGGGCCTTGTCGTCTCTTCTATCAACAATATCGCGGAAA 1200
ATGTTAATCACAAGACATACTGGCAGTTTCTTAGTGGTGTAACACCTTTG 1250
AATGAAGGGGTTGCTGACTACATACCCTTCAACCACGAGCACATCACAGC 1300
CAATTTCACACAGTACTAACGAAGAGGTGGGTTCAGCTTCTATCAAACAT 1350
CTCCAAAGGATGGGTGAAATTTTTTCCACTTCATTTTAAATCTATGCAAA 1400
AAAGCGAATGCCTGTGATGCTACCCCCGGG        1430

FIG. 1

STQTQSSCSVPSAQEPLVNGIQVLMENSVTSSAYPNPSILIAMNLAGAYN 50
LKAQKLLTYQLMSSDNNDLTIGQLGLTIMALTSSCRDPGDKVSILQRQME 100
NWAPSSPNAEASAFYGPSLAILALCQKNSEATLPIAVRFAKTLLANSSPF 150
NVDTGAMATLALTCMYNKIPVGSEEGYRSLFGQVLKDIVEKISMKIKDNG 200
IIGDIYSTGLAMQALSVTPEPSKKEWNCKKTTDMILNEIKQGKFHNPMSI 250
AQILPSLKGKTYLDVPQVTCSPDHEVQPTLPSNPGPGPTSASNITVIYTI 300
NNQLRGVELLFNETINVSVKSGSVLLVVLEEAQRKNPMFKFETTMTSWGL 350
VVSSINNIAENVNHKTYWQFLSGVTPLNEGVADYIPFNHEHITANFTQY 399

FIG. 2

TCTAGAAGAGAGGGAAGGAAGGGAAACGGAAAGAGAGAAAGAGAAAGAGA 50
AATGAAGAAGAATAGGATGATGATTATGATATGCAGTGTAGGAGTGGTGT 100
GGATGCTGTTAGTTGGAGGAAGCTACGGA 129

FIG. 3

TCTAGAAGCTCGTTGTTCATCTTAATTCTCCCAACAAGTCTTCCCATCAT 50
GTCTACCTCACATAAACATAATACTCCTCAAATGGCTGCTATCACACTCC 100
TAGGATTACTACTTGTTGCCAGCAGCATTGACATAGCAGGGCT 144

FIG. 4

| | |
|---|---|
| TCTAGAACTCACAACCTAGCTAGCTAGTAAACAGTATTTTCTATATACCA | 50 |
| AAAATGGCTTCAAGTTCCATAGCTCTTTTCTTGGCTCTCAATCTTCTCTT | 100 |
| TTTCACAACAATCTCCGCCGAGATGTGTGAAATACCAGAGATGGACAGCC | 150 |
| ATCTGGTAGAGAAGTTGGGCCAGCACCTCTTACCTTGGATGGACCGGCTT | 200 |
| TCCCTGGAGCACTTGAACCCCAGCATCTATGTGGGCCTACGCCTCTCCAG | 250 |
| TCTGCAGGCTGGGACCAAGGAAGACCTCTACCTGCACAGCCTCAAGCTTG | 300 |
| GTTACCAGCAGTGCCTCCTAGGGTCTGCCTTCAGCGAGGATGACGGTGAC | 350 |
| TGCCAGGGCAAGCCTTCCATGGGCCAGCTGGCCCTCTACCTGCTCGCTCT | 400 |
| CAGAGCCAACTGTGAGTTTGTCAGGGGCCACAAGGGGACAGGCTGGTCT | 450 |
| CACAGCTCAAATGGTTCCTGGAGGATGAGAAGAGAGCCATTGGGCATGAT | 500 |
| CACAAGGGCCACCCCCACACTAGCTACTACCAGTATGGCCTGGGCATTCT | 550 |
| GGCCCTGTGTCTCCACCAGAAGCGGGTCCATGACAGCGTGGTGGACAAAC | 600 |
| TTCTGTATGCTGTGGAACCTTTCCACCAGGGCCACCATTCTGTGGACACA | 650 |
| GCAGCCATGGCAGGCTTGGCATTCACCTGTCTGAAGCGCTCAAACTTCAA | 700 |
| CCCTGGTCGGAGACAACGGATCACCATGGCCATCAGAACAGTGCGAGAGG | 750 |
| AGATCTTGAAGGCCCAGACCCCCGAGGGCCACTTTGGGAATGTCTACAGC | 800 |
| ACCCCATTGGCATTACAGTTCCTCATGACTTCCCCCATGCCTGGGGCAGA | 850 |
| ACTGGGAACAGCATGTCTCAAGGCGAGGGTTGCTTTGCTGGCCAGTCTGC | 900 |
| AGGATGGAGCCTTCCAGAATGCTCTCATGATTTCCCAGCTGCTGCCCGTT | 950 |
| CTGAACCACAAGACCTACATTGATCTGATCTTCCCAGACTGTCTGGCACC | 1000 |
| ACGAGTCATGTTGGAACCAGCTGCTGAGACCATTCCTCAGACCCAAGAGA | 1050 |
| TCATCAGTGTCACGCTGCAGGTGCTTAGTCTCTTGCCGCCGTACAGACAG | 1100 |
| TCCATCTCTGTTCTGGCCGGGTCCACCGTGGAAGATGTCCTGAAGAAGGC | 1150 |
| CCATGAGTTAGGAGGATTCACATATGAAACACAGGCCTCCTTGTCAGGCC | 1200 |
| CCTACTTAACCTCCGTGATGGGGAAAGCGGCCGGAGAAAGGGAGTTCTGG | 1250 |
| CAGCTTCTCCGAGACCCCAACACCCCACTGTTGCAAGGTATTGCTGACTA | 1300 |
| CAGACCCAAGGATGGAGAAACCATTGAGCTGAGGCTGGTTAGCTGGTAGC | 1350 |
| CCGGG | 1355 |

FIG. 5

EMCEIPEMDSHLVEKLGQHLLPWMDRLSLEHLNPSIYVGLRLSSLQAGTK
EDLYLHSLKLGYQQCLLGSAFSEDDGDCQGKPSMGQLALYLLALRANCEF
VRGHKGDRLVSQLKWFLEDEKRAIGHDHKGHPHTSYYQYGLGILALCLHQ
KRVHDSVVDKLLYAVEPFHQGHHSVDTAAMAGLAFTCLKRSNFNPGRRQR
ITMAIRTVREEILKAQTPEGHFGNVYSTPLALQFLMTSPMPGAELGTACL
KARVALLASLQDGAFQNALMISQLLPVLNHKTYIDLIFPDCLAPRVMLEP
AAETIPQTQEIISVTLQVLSLLPPYRQSISVLAGSTVEDVLKKAHELGGF
TYETQASLSGPYLTSVMGKAAGEREFWQLLRDPNTPLLQGIADYRPKDGE
TIELRLVSW

FIG. 6

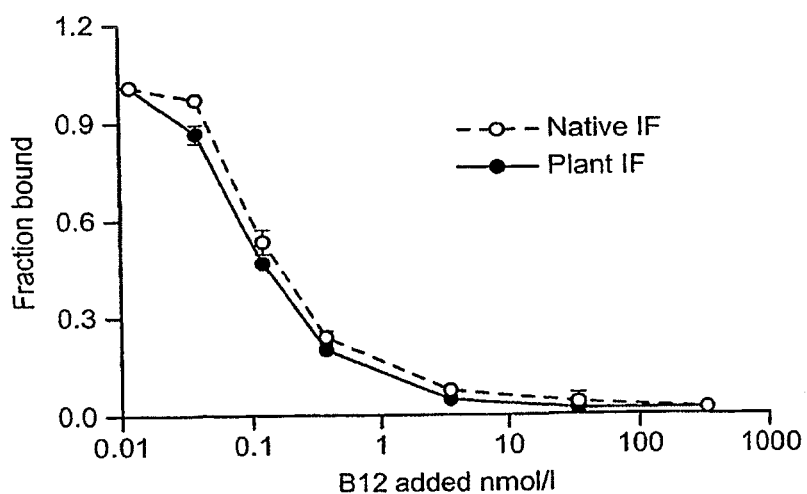

FIG. 7

TRANSGENIC PLANTS EXPRESSING COBALAMIN BINDING PROTEINS

FIELD OF THE INVENTION

The present invention generally relates to transgenic plant production of recombinant proteins which are able to bind cobalamin. The recombinant proteins may be used 1) prophylactically and/or therapeutically to treat cobalamin deficiency and 2) analytically.

REFERENCE TO SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821(f).

BACKGROUND OF THE INVENTION

Two groups of proteins are characterized by specific binding to vitamin B12, (cobalamin), hereafter called cobalamin binding proteins (CBP). One group consists of proteins involved in the assimilation of cobalamin and the other group is involved in the metabolism and utilization of cobalamin and includes the enzymes using cobalamin as a cofactor. Human assimilation of dietary cobalamin (Cbl) is a complex process with three successive Cbl-transporters involved: haptocorrin (HC), intrinsic factor (IF) and transcobalamin (TC) (1-4). These proteins strongly bind to Cbl which is synthesized by bacteria. The three CBPs provide uptake of the Cbl from the food to the body. IF is the main binder of Cbl in the intestinal tract and the IF-Cbl complex binds to an intestinal receptor resulting in the internalization of the Cbl to the blood (3,4). In the blood the TC-Cbl complex distributes assimilated Cbl among the tissues where it binds to one or more specific receptors present in the cell membrane (2,4). A significant amount of Cbl circulates in blood bound to HC (1,4). The exact function of HC is not identified. Inherited HC deficiency does not provoke any visible pathological effect (5) in contrast to the cases of IF- and TC-deficiencies (6,7).

Two Cbl dependent enzymatic reactions have been identified in mammals. The conversion of methylmalonyl-CoA to succinyl-CoA involves adenosyl-Cbl (Ado-Cbl) as a cofactor. Methyl-Cbl is a cofactor in the synthesis of methionine from homocysteine. Prior to the present invention, only small amounts of CBP have been isolated. Purification of Cbl binders is complicated by low concentration of these proteins in natural sources (1-4). Isolation of 1 mg of TC requires, for instance, 150-300 liters of human plasma (8,9). Human IF can be isolated from stomach juice which contains about 1 mg IF per liter. Isolation of pure TC and IF from natural sources is also complicated by the presence of relatively large amounts of HC in these sources. An expression system has been established for IF and TC in insect cells (10,11) and recombinant proteins were obtained at the level of 10-100 yg. We have expressed human and bovine TC in yeast and obtained 5-7 mg recombinant protein from a total of 1 liter of fermentation media (12). Human IF has been expressed in yeast and the yield was in the range of 1-4 mg per liter of total fermentation media (13). These expression systems are expensive to use and they deliver a mixture of holo- and apo-forms of the CBP. This is also the case for natural sources. The holo-form is the CBP in complex with Cbl, whereas the apo form is a CBP not complexed to Cbl. For use in diagnostic kits and other analytical purposes it is important to achieve purely either the apo- or holo-form of CBP.

IF isolated from human gastric juice is used for diagnostic purposes in the Schilling test where the patient ingests the isolated IF. Therefore, there is a risk for transmission of human diseases from the donor to the patient. Similarly, the use of IF isolated from pig or recombinant human IF isolated from the yeast expression media which contains an enzymatic hydrolysate of meat, may cause a risk for transmission of animal diseases to the patient. The use of recombinant human IF from a plant expression system will eliminate these problems.

Plants do not contain Cbl or CBPs. Therefore, recombinant plants with an inserted gene for i.e. human IF will express only the apo-form of IF. This makes plants very suitable as a "factory" for production of the apo-form of CBPs with no contamination of the holo-form. In other eukaryotic expression systems the recombinant CBP will be more or less saturated with Cbl resulting in a mixture of holo- and apo-form CBP. All other eukaryotic organisms except plants use Cbl in enzymatic reactions and therefore contain Cbl. Similarly, the use of transgenic plants results in recombinant CBP free of other CBPs since plants do not naturally express CBP. Isolation of IF from other sources, i.e. gastric juice results in a preparation contaminated with some HC since both CBPs are present in gastric juice.

CBPs expressed in plants but not other organisms are only in the apo-form and therefore the plant expression system gives the opportunity for purification of the CBP by affinity column chromatography with a cobalamin column. The holo-form of CBP does not bind to the cobalamin column. Therefore, CBPs expressed in plants are easier to purify than CBPs expressed in other organisms.

CBPs expressed in plants can be designed to have or alternatively not to have identical amino acid sequences as their corresponding native proteins. Posttranslational modifications such as disulphide bond formation between cystein residues will be present in the recombinant proteins. For CBPs with amino acid sequences identical with native CBPs the localization of disulphide bonds are expected to be identical, since CBPs from plants binds Cbl. Therefore the tertiary structure of recombinant CBPs are expected to be identical to native CBPs. The specific binding of recombinant human IF (rhIF) from plants in a complex with Cbl to the intestinal receptor cubilin, support an identical tertiary structure between native hIF and rhIF from plant. The glycosylation of recombinant CBPs from plants will not be identical to the glycosylation of the corresponding native CPBs, since glycosylation is cell type specific. Therefore, rhIF from plants differ from native IF by the composition of the sugars in the carbohydrate chains.

The plant expression system will be very useful for large scale production of CBP, since the growth of recombinant plants is low-tech and furthermore, it is simple to scale up the production of recombinant protein by simply planting more land. The plant expression system gives the opportunity to use large amounts of recombinant CBP in therapeutic programs, e.g. elderly people with reduced uptake of vitamin B-12. Furthermore, the CBP may be used after no or very little purification since many plant species, useful for transgenic expression of proteins, are used for human consumption e.g. maize, potato, barley, rice, carrot.

A need exists for a better way to produce these CBPs.

BRIEF DESCRIPTION OF THE INVENTION

Thus the present invention provides a transgenic plant that expresses at least one protein capable of binding cobalamin and/or analogs thereof. A "cobalamin" (Cbl) is a molecule that consists of a corrin ring with four pyrrole units which surround and bind to the essential and central cobalt atom. Below the corrin plane is a nucleotide derivative with a dimethylbenzimidazole base, which also is linked to the cobalt atom.

Finally the cobalt atom binds to a sixth molecule (e.g.: —$CH_3$, OH—, $H_2O$, 5'-deoxyadenosyl, CN) located above the corrin plane. Cyanocobalamin is referred to as vitamin B12, but other cobalamins have identical nutritional properties. Cobalamin cannot be synthesized by animals or plants and is only produced by some micro-organisms, in particular, anaerobic bacteria. A "cobalamin analog" is a cobalamin molecule where, for example, the nucleotide unit has been changed or partially removed as in cobinamid. The cobalamin analog may also be a cobalamin linked to another functional molecule, eg a cytotoxin. A "cobalamin binding protein" is a protein which can bind a cobalamin, e.g. the human proteins: intrinsic factor, transcobalamin, haptocorrin, methylmalonyl-CoA mutase and methionine synthetase. A "transgenic plant" is a plant where some or all of its cells contain an expression vector or a fragment of an expression vector.

In a first preferred embodiment the protein capable of binding cobalamin or analogs thereof would be any one of transcobalamin, intrinsic factor, haptocorrin, methylmalonyl-CoA mutase, methionine synthase or a protein with at least 60% identity to any one of these proteins or a fragment thereof. The percent identity of two amino acid sequences or of two nucleic acid sequences is determined by aligning the sequences for optimal comparison purposes (e.g., gaps can be introduced in both sequences for best alignment) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=# of identical positions/total # of positions×100).

The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-6877. The NBLAST and XBLAST programs of Altschul, et al. (1990) J. Mol. Biol. 215: 403-410 have incorporated such an algorithm. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilised as described in Altschul et al. (1997) Nucleic Acids Res. 25: 3389-3402. Alternatively, PSI-Blast can be used to perform an iterated search which detects distant relationships between molecules (Id.). When utilising BLAST, Gapped BLAST, and PSI-Blast programs, the default parameters of the respective programs (e.g., XBLAST and NBLAST) can be used. See www.ncbi.nlm.nih.gov.

Another example of a mathematical algorithm utilised for the comparison of sequences is the algorithm of Myers and Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis and Robotti (1994) Comput. Appl. Biosci, 10:3-5; and FASTA described in Pearson and Lipman (1988) Proc. Natl. Acad. Sci. 85:2444-8. Within FASTA, ktup is a control option that sets the sensitivity and speed of the search.

However, the important factor is that a protein with a similar sequence identity to natural CBP is also functionally the same as the CBP binding proteins. In other words, the proteins produced according to the present invention are able to make a complex with Cbl and bind to the corresponding CBP receptor.

The plant is preferably a "Generally Recognised As Safe" (GRAS) plant. Plants that only produce pollen in the second year of the life cycle such as carrots can be used to prevent cross contamination of other plants in the environment with genetically modified material.

A whole plant can be regenerated from the single transformed plant cell by procedures well known in the art. The invention also provides for propagating material or a seed comprising a cell. The invention also relates to any plant or part thereof including propagating material or a seed derived from any aspect of the invention.

In a second aspect the present invention provides a cobalamin binding protein that is expressed in a transgenic plant, or by transgenic plant cell culture. This protein is preferably isolated or purified from the plant material. This protein can be either in the apo- (i.e. not bound to cobalamin) or holo-form (i.e. bound to cobalamin). The protein that is produced by the transgenic plant has different carbohydrate moieties attached to the molecule compared to a similar protein produced by humans or micro-organisms such as yeast. The variation in the carbohydrate content of the proteins can be seen by the different apparent molecular weights of the protein produced by the transgenic plant as compared to the protein produced by humans or yeast. Once the proteins are stripped of the carbohydrate groups, all the proteins have the same molecular weight as seen by SDS-Polyacrylamide gel electrophoresis.

In a third aspect the present invention provides a method of isolating and/or purifying the cobalamin binding protein or a functional fragment thereof as defined above comprising the following steps: (a) Homogenisation of the transgenic plant material; (b) Filtration of the supernatant formed by centrifugation of the homogenate; (c) Affinity column chromatography using cobalamin (d) Elution of the cobalamin binding protein attached to cobalamin (e) Gel filtration; And optionally further comprising the following steps to produce the apo-form of the cobalamin binding protein: (f) Dialysis against 5M guanidine HCL; (g) Dialysis against 0.2M sodium phosphate.

In a fourth aspect the present invention provides a composition comprising a cobalamin binding protein of the present invention. The cobalamin binding protein can be provided in a substantially pure form. Alternatively, it can be provided as transgenic plant material which is raw, unprocessed transgenic plant material or more or less processed transgenic plant material that is ingested e.g. in the form of chopped, ground, homogenized transgenic plant material, liquid transgenic plant extract as well as partially or completely purified recombinant CBP.

The composition is preferably a pharmaceutical composition. The compositions of the invention may be adapted for administration by any appropriate route, for example by the oral (including buccal or sublingual) route. Such formulations may be prepared by any method known in the art of pharmacy, for example by bringing into association the active ingredient with the carrier (s) or excipient (s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Preferred unit dosage formulations are those containing a daily dose or sub-dose, as herein above recited, or an appropriate fraction thereof, of an active ingredient.

It should be understood that in addition to the ingredients particularly mentioned above, the formulations may also include other agents conventional in the art having regard to the type of formulation in question, for example those suitable for oral administration may include flavouring agents. The recombinant plant CBP may also be delivered in combination with a second component like cobalamin or cobalamin analogs or cobalamin containing a tracer atom (or molecule). Tablets with recombinant plant CBP with or without a second component may also be designed for the release of CBP in the intestine to avoid the low gastric pH and the gastric proteases.

Preferably, the compositions of the invention are presented for oral use. The recommended daily dose for vitamin B12 is 2.5 micrograms which corresponds to 125 micrograms of IF-Cbl or 122.5 micrograms of IF.

In a fifth aspect the present invention provides a foodstuff comprising transgenic plants of the invention or plant material derived from such plants.

In a sixth aspect the invention provides a method for treating cobalamin deficiency comprising administration of a composition that includes at least one cobalamin binding protein of the present invention. The deficiency can be overcome by providing additional amounts of the proteins involved in vitamin B12 uptake and transport. These proteins are preferably any one or more of transcobalamin, haptocorrin and intrinsic factor. The proteins can be administered alone i.e. in the apo-form, or in conjunction with cobalamin or a cobalamin analog i.e. in the holo-form. A "holo-form" of a cobalamin binding protein is a complex of the cobalamin binding protein and its ligand e.g. cobalamin or a cobalamin analog. An "apo-form" of a cobalamin binding protein is the cobalamin binding protein which is ready to bind a cobalamin or a cobalamin analog.

In a seventh aspect the invention provides CBP of the invention for use in diagnostic tests. In such tests the content of cobalamins in for example blood is detected by the ability of the extracted biological sample to compete with tracer Cbl for binding to CBP as described by Nexo and Gimsing, 1981, Scand. J. Clin. Lab. Invest. 41: 465468; "Insolubilized pure human intrinsic factor used for quantitation of cobalamins in serum". In other tests the purpose is to measure the CBP, either its total content or its holo- or apo-form. Such tests can be performed by for example enzyme linked immunosorbent assay (ELISA) directly (Nex et al. 2000, Clinical Chemistry 46 (10): 1643-1649), or in combination with a pretreatment of the sample that removes the apo-form i.e as described by Next, 1975, Biochim. Biophys. Acta, 379: 189-192.

In another aspect the present invention provides a method for quantifying cobalamin absorption from the intestine by means of a Schilling test utilizing IF or a functional fragment thereof that has been isolated from a transgenic plant expressing the cobalamin binding protein or a functional fragment thereof. For example, a "Schilling test" may be performed by using a dose of Cbl with radioactive cobalt for oral ingestion followed by 24 hours of urine collection and measurement of the fraction of radioactive Cbl in the urine. If no radioactive Cbl is detected in the urine of this first stage of the test, a second test is performed a week later. Now the test uses a dose of Cbl with radioactive cobalt together with IF for oral ingestion followed by 24 hours of urine collection and measurement of the fraction of radioactive Cbl in the urine (Fairbanks, V. F. Test for pernicious anaemia: the "Schilling test" Mayo Clin Proc. 1983, 58:541-544).

In a further aspect the invention provides a method for quantifying cobalamin or analogs thereof utilizing the protein of the present invention. The isolated CBP produced by the transgenic plant can be used for example in a competitive binding assay utilizing labeled cobalamin or analogues thereof.

In yet a further aspect the present invention provides a method for quantifying CBP utilizing the protein of the present invention. The CBP of the present invention can be isolated and then labeled radioactively, and used in a competitive binding assay with cobalamin or an analog thereof.

In yet another aspect the present invention provides a method for quantifying receptors for cobalamin binding proteins utilizing the protein of the present invention. For example the rhIF may be complexed with a labeled cobalamin molecule e.g. radioactive cobalmin, to determine the number or binding capacity of the intestinal IF-B 12 receptor.

In a further aspect the present invention provides a nucleic acid construct comprising nucleic acid coding for one or more cobalamin binding proteins, operably linked to one or more regulatory sequences capable of directing expression in a plant. The regulatory sequence can, for example, be a promoter such as 35S CaMV. In addition a signal peptide sequence such as the *Arabidopsis thaliana* extensin signal peptide, Phalseolus vulgaris chitinase signal peptide, or *Nicotiana tabacum* glucan beta-1,3-glucanase can also be included. In one preferred embodiment the nucleic acid is DNA.

In yet another aspect the present invention provides a vector comprising a nucleic acid construct of the invention. The vector may be a plasmid, cosmid or phage. Vectors frequently include one or more expressed markers which enable selection of cells transfected, or transformed, with them and preferably, to enable a selection of cells, containing vectors incorporating heterologous DNA. If the vector is intended for expression, sufficient regulatory sequences to drive expression will be present. The nucleic acid and promoter sequences according to the invention are preferably for expression in plant cells.

In yet a further aspect the invention also provides a plant cell comprising a nucleic acid sequence of the invention and/or a vector of the invention. The cell may be termed as a "host" which is useful for manipulation of the nucleic acid, including cloning. Alternatively, the cell may be a cell in which expression of the nucleic acid is obtained, most preferably a plant cell. The nucleic acid can be incorporated into cells by standard techniques known in the art. Preferably, nucleic acid is transformed into plant cells using a disarmed Ti plasmid vector carried in *agrobacterium* by procedures known in the art, for example, as described in EP-A-0116718 and EP-A-0270822. Foreign nucleic acid can alternatively be introduced directly into plant cells using an electrical discharge apparatus or by any other method that provides for the stable incorporation of the nucleic acid into the cell. Nucleic acid of the present invention preferably contains a second "marker" gene that enables identification of the nucleic acid. This is most commonly used to distinguish the transformed plant cells containing the foreign nucleic acid from other plant cells that do not contain the foreign nucleic acid. Examples of such marker genes include antibiotic resistance, herbicide resistance and glucoronidase (GUS) expression. Expression of the marker gene can be controlled by a second promoter, which allows expression of the marker gene in all cells.

The foreign nucleic acid is preferably introduced into only the mitochondria and/or the chloroplasts of the host cell. The nucleic acid may be become introduced into the genome, within the nucleus, or in other organelles, including mitochondria or plastids such as protoplastids, chromoplasts or leucoplasts. Pollen does not contain plastids or mitochondria. Therefore, by only having the foreign nucleic acids within these organelles, this will prevent the transfer of transgenic material to wild type plants in the surrounding environment by cross pollenation.

The aim of the present invention is to produce recombinant cobalamin binding proteins (CBP) in plants. Plants do not contain or use cobalamin and therefore the recombinant CBP expressed in plants will all be in the apo-form (not complexed with cobalamin) whereas CBP from natural sources are a mixture of holo- and apo-form CBP. Unlike use of transgenic plants, production of a particular CBP from natural sources involves further purification from other CBPs. Furthermore, transgenic plants provide a cheap method for large scale production of CBP, as compared to all other known sources of the proteins.

The present invention will be easy to scale-up for production of large quantities of recombinant CBP by simply planting larger areas of land with the CBP producing plants. This is relatively cheap compared to production of CBP in high technology demanding fermentors and incubators when yeast or insect cells are used.

The use of natural sources to isolate CBP has some limitations. Because of the relatively low concentrations of TC in blood and milk this protein is very expensive for isolation in large scale. Isolation of IF is performed from porcine stomach in large scale and to a lesser extent from rat stomach and human stomach juice. Since HC is also present in the stomach, a high degree of purification is needed to separate these CBP when IF is used for diagnostic kits. For example, IF free of Cbl is requested (FDA requirement) for use as a binding protein in assays of Cbl in plasma. In addition to these problems natural sources also constitute a serious risk for transmission of diseases to patients receiving the CBP. Expression of recombinant CBP in transgenic plants will result in extracts with no other CBP than the recombinant CBP. Furthermore the risk of transmitting animal or human diseases from natural sources of CBP to patients is eliminated by the use of CBP from transgenic plants. Plant expression systems also give the opportunity to use GRAS (Generally Recognized As Safe) organisms as host for the production of CBP.

As examples of the use of transgenic plants as an expression system for production of CBPs, we have expressed human IF and human TC in the plant *Arabidopsis thaliana*. We tested the transgenic plants for cobalamin binding capacity (CBC) as described by (14).

The description of the invention hereafter refers to *Arabidopsis thaliana*, when necessary for the sake of example. However, it should be noted that the invention is not limited to genetic transformation of plants such as *Arabidopsis thaliana*. The method of the present invention is capable of being practiced for other plant species, using methods/techniques well known to those skilled in the art.

BRIEF DESCRIPTION OF THE DRAWINGS

The invention will now be described with reference to the following examples, which should not be construed as in any way limiting the invention.

The examples refer to the figures in which:

FIG. 1 shows the nucleotide sequence encoding extensin signal peptide sequence fused to the mature human intrinsic factor encoding region and part of the 3'-untranslated region (SEQ ID NO:2). This nucleotide sequence is a fusion of a nucleotide sequence (position 7-119) adopted from GenBank accession no. AF104327 which encodes an *Arabidopsis thaliana* extensin-like signal peptide with the amino acid sequence MASSSIALFLALNLLFFTTISA (SEQ ID NO:1). The methionine start codon (ATG) of this signal peptide sequence is underlined. The nucleotide sequence encoding mature human intrinsic factor (position 120-1316) is shown in bold letters and adopted from GenBank accession no X76562. This sequence is followed by a translational stop codon (TAA) which is underlined and a nucleotide sequence from the 3'-untranslated region of the intrinsic factor mRNA. The underlined restriction sites XbaI (position 1-6) and XmaI (position 1425-1430) was introduced to facilitate cloning in the plant transformation vector.

FIG. 2 shows the amino acid sequence of mature human intrinsic factor which was encoded by the nucleotide sequence shown in bold letters in FIG. 1 at position 120-1316 (SEQ ID NO:4).

FIG. 3 shows a nucleotide sequence (SEQ ID NO:5) at position 7-129 from *Phaseolus vulgaris* CH5B-chitinase, GenBank accession no. S43926 and it encodes a signal peptide with the amino acid sequence MKKNRMMIMICSVGVVWMLLVGGSYG (SEQ ID NO:6). This nucleotide sequence was fused to the nucleotide sequence shown in bold letters in FIG. 1 that encodes the mature human intrinsic factor. The XbaI restriction site used for cloning is underlined at position 1-6 and the translational start codon ATG is underlined at position 52-54.

FIG. 4 shows a nucleotide sequence (SEQ ID NO:7) at position 7-144 from *Nicotiana tabacum* glucan beta-1,3-glucanase gene, GenBank accession no. M60402 and it encodes a signal peptide with the amino acid sequence MSTSHKHNTPQMAAITLLGLLLVASSIDIAGA (SEQ ID NO:8). This nucleotide sequence was fused to the nucleotide sequence shown in bold letters in FIG. 1 that encodes the mature human intrinsic factor. The XbaI restriction site is underlined (position 1-6) and the translational start codon ATG is underlined at position 49-51.

FIG. 5 shows the nucleotide sequence (SEQ ID NO:9) encoding the extensin signal peptide sequence fused to the mature human transcobalamin encoding region. This nucleotide sequence is a fusion of a nucleotide sequence (position 7-119) adopted from GenBank accession no. AF104327 which encodes an *Arabidopsis thaliana* extensin-like signal peptide with the amino acid sequence MASSSIALFLALNLLFFTTISA (first 22 amino acids of SEQ ID NO:3). The methionine start codon (ATG) of this signal peptide sequence is underlined. The nucleotide sequence encoding mature human transcobalamin (position 120-1346) is shown in bold letters and adopted from GenBank accession no 000355. This sequence is followed by a translational stop codon (TAG) at position 1347-1349 which is underlined. The underlined restriction sites XbaI (position 1-6)

and XmaI (position 1350-1355) was introduced to facilitate cloning in the plant transformation vector.

FIG. 6 shows the amino acid sequence (SEQ ID NO:11) of mature human transcobalamin which was encoded by the nucleotide sequence shown in bold letters in FIG. 5 at position 120-1346.

FIG. 7 shows the native intrinsic factor (o) present in human gastric juice and recombinant human intrinsic factor extracted from transgenic plants of *Arabidopsis thaliana* (g) which were compared concerning their ability to bind cobalamin or cobinamid. Equal amounts of the respective proteins were added to a mixture containing a fixed amount of cobalt (57Co) labelled cobalamin mixed with increasing amounts of non-radioactive cobalamin or cobinamide (X axis). Free and bound ligand were separated and the amount of 57Co attached to the protein was measured in a gamma counter. The 57Co fraction bound relative to the amount of 57Co bound in the absence of unlabeled cobalamin or cobinamide was calculated (Y axis). The figure shows that recombinant IF behaves as does native IF with specificity for binding cobalamin but not cobinamid.

FIG. 8 shows how polyclonal antibodies against human gastric intrinsic factor and alkaline phosphatase-conjugated immunoglobulins were used to visualize intrinsic factor on a Western blot containing proteins separated by SDS-PAGE. Transgenic *Arabidopsis thaliana* plants expressing recombinant human intrinsic factor were harvested and homogenized in 0.2 M phosphate buffer before centrifugation and analysis of the supernatant. For comparison transgenic yeast (*Pichia pastoris*) containing an insert of human intrinsic factor was used for expression of recombinant human intrinsic factor. Secreted proteins form the fermentation media were precipitated with ammonium sulfate (80% w/v) before dialysis against 20 mM Tris pH 8.0 and analysis. Purified human gastric intrinsic factor was also used for comparison. An aliquot of each sample was treated with the enzyme PNGaseF to remove carbohydrate from the proteins. Lane: "Plant IF" contains the proteins from the plant extract; "Plant IF+PNGaseF" contains the proteins from the plant extract treated with PNGaseF; "Yeast IF" contains yeast protein; "Yeast IF+PNGaseF contains yeast protein treated with PNGaseF; "Human gastric IF" contains purified human IF and "Human gastric IF+PNGaseF" contains purified human IF treated with PNGaseF. The arrow marks the 45 kDa band with deglycosylated IF from the three samples treated with PNGaseF.

The blot shows that the glycosylated form of IF from the three samples have significant differences in molecular weight but the deglycosylated samples contain mature IF with the same molecular weight.

Figure 9:
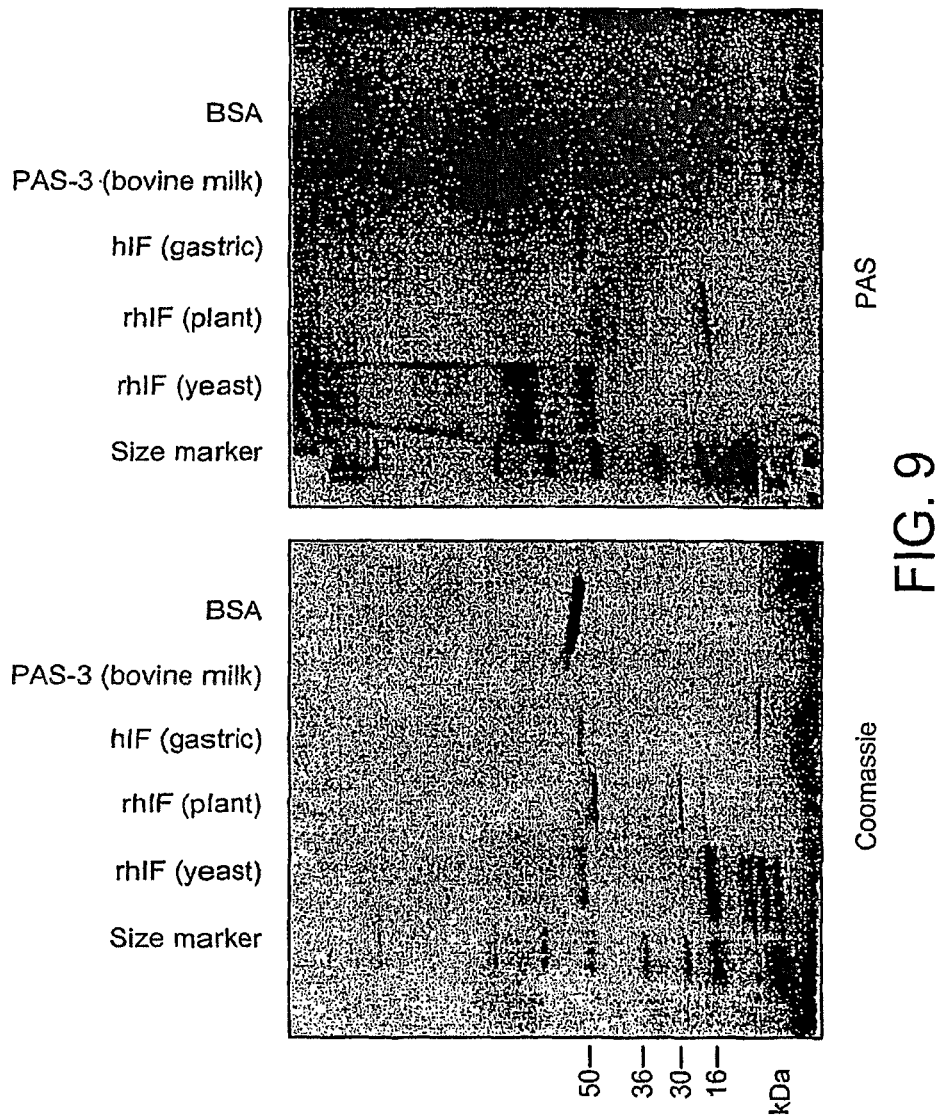

FIG. 9 compares the glycosylation and molecular weight of intrisicic factor prepared from various sources. PAS staining was used to visualize glycoproteins. Recombinant human intrinsic factor (rhIF) from transgenic plants (*Arabidopsis thaliana*) and transgenic yeast (*Pichia pastoris*) were isolated and purified by affinity chromatography on a column with cobalamin. Purified human gastric IF was used for comparison. Bovine PAS-3 is heavily glycosylated and function as a control for PAS staining. Bovine serum albumin (BSA) has no glycosylation and function as a "negative" control for PAS staining. The samples were run in SDS-PAGE in duplicate gels. The second gel was stained with coomassie brilliant blue.

The gels show that recombinant plant IF is glycosylated since an approximately 50 kDa rhIF band from transgenic plants is stained with PAS.

Figure 10:
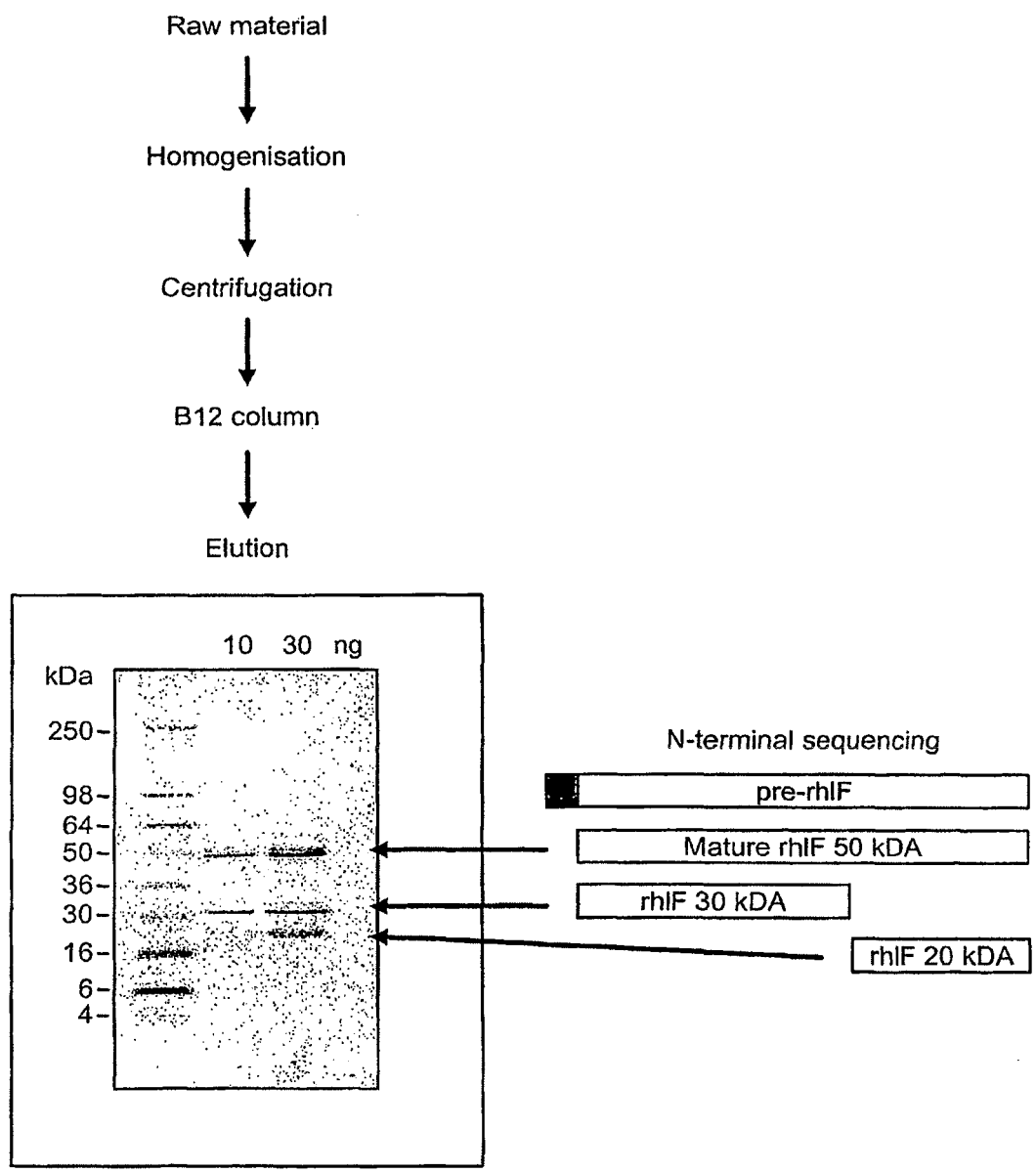

FIG. 10 shows the purification method for isolating rhIF and a blot of the protein fragments used for N-terminal sequencing. Purified recombinant human intrinsic factor (rhIF) was run by SDS-PAGE, blotted onto a PVDF-membrane and stained with coomassie brilliant blue. The mature rhIF and the partially cleaved rhIF fragments (proteases present in *Arabidopsis thaliana* cleave rhIF) were analyzed by amino acid sequencing. N-terminal sequencing of the three fragments marked with arrows showed that the approximately 50 kDa fragment has the same N-terminus as mature human gastric intrinsic factor. The lower two fragments (30 and 20 kDa) are a result of a proteolytic split in front of amino acid residue 285 of mature hIF.

Figure 11:
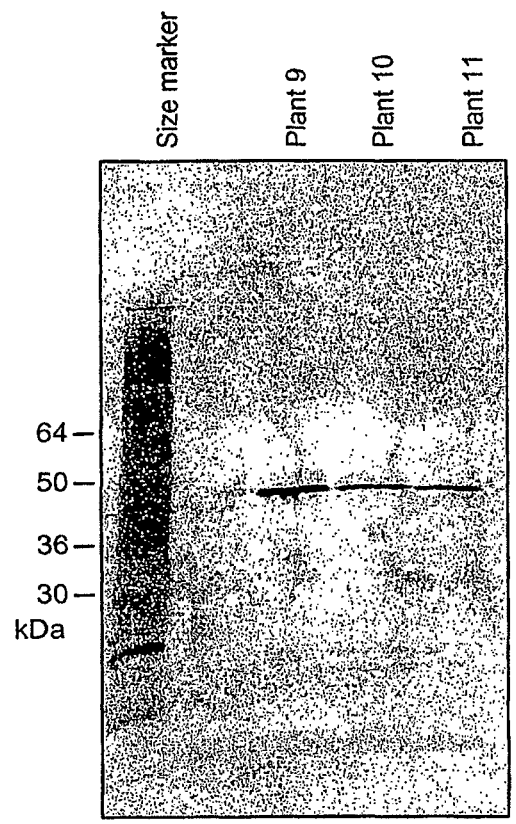

FIG. 11 shows the expression of transcobalamin in transgenic plants. Polyclonal antibodies against human transcobalamin (TC) and alkaline phosphatase-conjugated immunoglobulins were used to visualize TC on a Western blot containing proteins separated by SDS-PAGE. Transgenic *Arabidopsis thaliana* plants (no 9-11) expressing recombinant human TC were harvested and homogenized in 0.2 M phosphate buffer before centrifugation and analysis of the supernatant.

Figure 12:
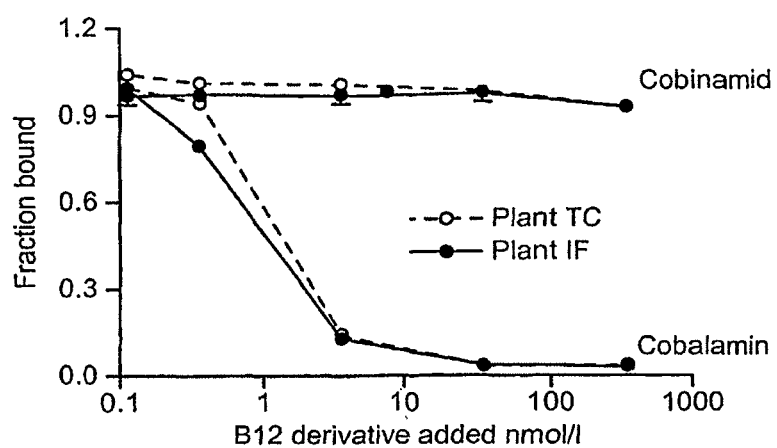

The blot shows a single protein with the expected molecular size of 45 kDa in each of the three plants FIG. 12 shows the ability of plant recombinant human transcobalamin (o) and plant recombinant human intrinsic factor (g) to bind cobalamin or cobinamid. Both recombinant proteins were extracted form transgenic *Arabidopsis thaliana* plants. Equal amounts of the respective proteins were added to a mixture containing a fixed amount of cobalt (57Co) labeled cobalamin mixed with increasing amounts of nonradioactive cobalamin or cobinamide (X axis). Free and bound ligand was separated and the amount of 57Co attached to the protein was measured in a gamma counter. The 57Co fraction bound relative to the amount of 57Co bound in the absence of unlabelled cobalamin or cobinamide was calculated (Y axis). The figure shows that recombinant human intrinsic factor and recombinant human transcobalamin both bind cobalamin but not cobinamid.

Figure 13:
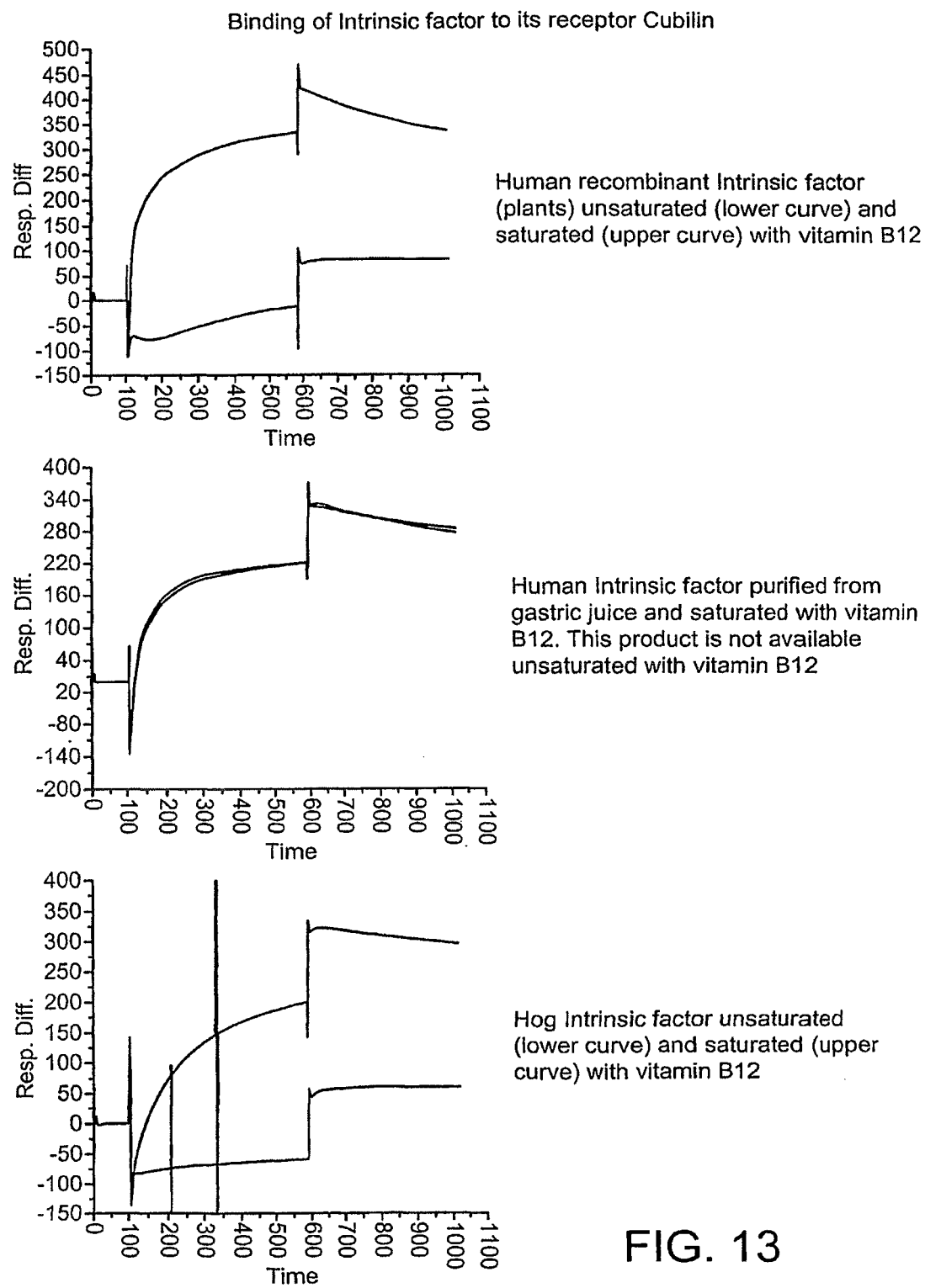

FIG. 13 shows the binding of intrinsic factor to the human intestinal receptor protein cubilin. The binding between intrinsic factor and its receptor cubilin was analysed employing a BIAcore 2000 instrument (Biacore AB, Uppsala, Sweden). An increase in Resp. Diff. (Y axis) indicates binding between intrinsic factor and cubilin. At time approximately 100 a solution with intrinsic factor is added to the immobilized cubilin. Intrinsic factor was isolated from transgenic plants, human gastric juice and hog stomach. Preparations of vitamin B 12 saturated and vitamin B12 unsaturated intrinsic factor were used. At time approximately 600 intrinsic factor is removed from the solution and the dissociation between cubilin and intrinsic factor is followed. The results indicate that recombinant intrinsic factor-like native intrinsic factor-binds to cubilin only when saturated with vitamin B12 and that the binding characteristics for recombinant and native intrinsic factor are alike.

DETAILED DESCRIPTION OF THE INVENTION

Example 1

As shown in FIG. 1, the extensin signal peptide encoding nucleotide sequence from *Arabidopsis thaliana* was fused to the nucleotides encoding mature human intrinsic factor (FIG. 2). This construct was inserted in the plant transformation vector CRC179.

Construction of the CRC-179 Vector

The vector pPZP 211 (Hajdukiewicz, P; Svab, Z; & Maliga, P. 1994 Plant Mol. Biol. 25, 989-994) was digested with EcoRI and KpnI and a pAnos sequence was released from pGPTV KAN (Becker, D; Kemper, E; Schell, J &

Masterson, R. 1992 Plant Mol Biol 20, 1195-1197) by the same set of enzymes and cloned into the pPZP 211 vector. The resulting vector was digested with PstI and KpnI and blunt-ended. A blunt-ended EcoRI and HindIII fragment containing the 35S CaMV promoter from the vector described in Jefferson, R A; Kavanagh, T A & Bevan, M W. 1987 EMBO J. 6, 3901-3907 was cloned into the blunt-ended vector. This vector was named CRC-179.

The bacteria *Agrobacterium tumefaciens* was transformed with this recombinant vector.

Culture of *Agrobacterium tumefaciens*

The *Agrobacterium tumefaciens* strain used was GV3101 (pMP90) (Koncz and Schell, 1986) carrying the binary plasmid CRC-179 with an insert encoding a CBP cloned into the XbaI-XmaI sites. The insert sequences are shown in the FIGS. 1,3, 4, & 5. The bacteria were grown to stationary phase in 200 ml liquid culture at 28-30 C, 250 rpm in sterilized LB media (10 g tryptone, 5 g yeast extract, 5 g NaCl per liter water) carrying added rifampicin (100 mg/ml), streptomycin (100 mg/ml) and gentamycin (50 mg/ml). Cultures were started from a 1:200 dilution of a smaller overnight culture and grown for 16-18 hours. Bacteria cells were harvested by centrifugation for 10 min at 5500 g at room temperature and then resuspended in 400 ml inoculation medium (10 mM MgCl2, 5% w/v sucrose and 0.05% v/v Silwet L-77 (Lehle Seeds, Round Rock, Tex., USA)).

The recombinant *A. tumefaciens* bacteria were used to transform *Arabidopsis thaliana* plants.

Transformation of *Arabidopsis* Plants

The *Arabidopsis* plants were transformed by the floral dip method (Clough and Bent, 1998).

Plant Growth

*Arabidopsis* plants (ecotype Col-0) were grown to flowering stage in growth chamber, 20 C day/18 C night with LiCl lighting for 18 h/day, humidity 70%. Between 20 and 25 plants were planted per 64 cm2 pot in moistened soil mixture consisting of: 40 kg soil orange and 40 kg soil green (Stenrgel Mosebrug A/S Kjellerup, DK), 25 liter 4-8 mm Fibroklinker (Optiroc, Randers, DK), 12 liter Vermiculite (Skamol, DK) and 300 g Osmocote plus NPK 15-5-11, 3-4 months (Scott's, UK).

To obtain more floral buds per plant, inflorescences were clipped after most plants had formed primary bolts, relieving apical dominance and encouraging synchronized emergence of multiple secondary bolts. Plants were dipped when most secondary inflorescences were about 7-13 cm tall (7-9 days after clipping).

The transgenic *Agrobacterium* suspension was added to a 400 ml beaker and plants were inverted into the suspension such that all above-ground tissues minus the rosette were submerged. The plants were removed after 10-15 sec of gentle agitation and placed in horizontal position in a sealed plastic bag for 24 hours at room temperature. After 24 hours the plants were moved to the growth camber and the plastic bags were removed. Plants were grown 3-4 weeks until siliques were brown and dry. Seeds were harvested and allowed to dry at room temperature for 7 days.

Selection of Transformants

Seed were surface sterilized by a treatment with 0.5% sodium hypochlorite containing 0.05% v/v Tween 20 for 7 min, then with 70% ethanol for 2 min, followed by three rinses with sterile water.

To select for transformed plants the sterilized seeds were plated on kanamycin selection plates at a density of approximately 2000 seeds per 144 cm2 and grown for 8-10 days at 21 C under light for 16 hours per day. Selection plates contained 1×MS medium (Duchefa, Haarlem, NL #M 0222), 1% w/v sucrose, 0.9% w/v agar noble (Difco, Detroit, USA), 50 mg/ml kanamycin, pH 5.7. After selection the transformed plants were transferred to growth chambers (see Plant growth).

Seeds from these infected plants were planted and recombinant plants were identified by western-blotting analysis. Seeds from recombinant plants were used to grow new recombinant plants called IF-plants.

One kilogram of three week old IF-plants was homogenization with 2 liters of phosphate buffer and clarified by centrifugation. This extract contained 100 mg recombinant human IF with CBC. This IF had specificity for cobalamin binding whereas the analog cobinamid was not bound by the IF as tested by the method described by (15). FIG. 7 shows that the rhIF from plants and native human gastric IF have the same specificity for binding Cbl, but not cobinamid.

The transgenic plants were analyzed as described by (16) and shown to contain no cobalamin. This shows that the plant rhIF was at the apo-form. Analysis of the protein from these transgenic plants showed that they express a protein of approximately 50 kDa as recognized on a Western-blot with antibodies against human IF (see FIG. 8,10). Amino acid sequencing of the N-terminal region of this 50 kDa protein showed the same sequence as that present in mature natural IF (FIG. 2). Therefore, the post-translational cleavage of the extensin signal peptide from the fusion protein results in the secretion of a recombinant IF with the correct N-terminus. The size of approximately 50 kDa indicates that the protein was full-length. A mature full-length IF is 399 amino acids with a calculated molecular weight of 43412 Da. The recombinant IF contains some carbohydrates as shown by PAS-staining of blotted recombinant protein separated by SDS-PAGE (see FIG. 9). Deglycosylation of rhIF from plants results in a protein with an approximately similar observed and calculated molecular weight (FIG. 8). The molecular size of natural human IF was approximately 5 kDa larger than the recombinant plant IF as estimated from the western-blot. Some difference in the carbohydrate composition is expected between natural human IF and recombinant plant IF since carbohydrate composition is tissue specific and to some extent unique to each individual. Differences in the molecular weight between natural and recombinant IF may therefore be a result of different carbohydrate composition. This was shown by removal of the carbohydrates from human gastric IF, human IF expressed in yeast and human IF expressed in plants. The deglycosylated form of these three IF proteins to have the same molecular weight (see FIG. 8).

On a Western-blot containing purified rhiF from transgenic *Arabidopsis thaliana*, two minor bands of approximately 30 and 20 kDa were observed in addition to the 50 kDa band with mature rhiF (FIG. 10). N-terminal sequencing of these two bands showed, that the 30 kDa band contained the N-terminal sequence of mature human IF. The 20 kDa band contained an N-terminus located at glycine-285 of mature IF. The calculated molecular weight of the fragment containing amino acid residues 1-284 was 30612 Da and the fragment containing amino acid residues 285-399 had a calculated molecular weight of 12817 Da. The inconsistency between the observed 20 kDa and the calculated 12817 Da most likely was a result of glycosylation of one or more of the four potential N-linked glycosylation sites of the fragment containing amino acid residue 285-399. The PAS-staining also recognized the 20 kDa band showing that some glycosylation was present on the fragment. No PAS-staining was observed for the 30 kDa fragment although one potential N-linked glycosylation site was present on this fragment. This is consistent with that no difference was found between the observed and calculated molecular weight for the fragment containing amino acid residues 1-284.

FIG. 13 shows that rHIF from plants in complex with vitamin B12 binds to the human intestinal receptor protein cubilin. The apo-form of rHIF does not bind to the cubulin receptor. For comparison binding of human gastric IF and hog IF were also shown to bind to the cubulin receptor only when in holo-form. These results show, that recombinant human intrinsic factor from plants behaves as native gastric intrinsic factor with respect to receptor binding.

Example 2

Arabidopsis thaliana was transformed with a vector construct which contained a nucleotide sequence encoding the signal peptide from the Phaseolus vulgaris chitinase CH5B fused to the nucleotide sequence encoding mature human intrinsic factor (FIG. 3). This construct was used to generate transgenic Arabidopsis thaliana plants. These plants were shown to contain CBC at the same level as most of the extensin-IF plants showing that the choice of signal peptide for intrinsic factor expression is not restricted to one sequence.

Example 3

Arabidopsis thaliana was transformed with a vector construct which contained a nucleotide sequence encoding the signal peptide from the Nicotiana tabacum glucan beta-1, 3-glucanase fused to the nucleotide sequence for mature human intrinsic factor (FIG. 4). This construct was used to generate transgenic Arabidopsis thaliana plants. These plants were shown to contain CBC at the same level as most of the extensin-IF plants showing that the choice of signal peptide for intrinsic factor expression is not restricted to one sequence.

Conclusions from IF-Plants in Examples 1-3

As far as we have tested the recombinant human IF from plants it behaves as natural human gastric IF concerning its mature N-terminus, recognition by anti-IF antibodies, binding of cobalamin, lack of cobinamide binding, binding to the intestinal receptor, and presence of carbohydrates. In contrast to gastric juice where IF is present together with another CBP, haptocorrin, and to some extent cobalamin from the food, transgenic IF plants contain no cobalamin or other CBP than IF. The glycosylation of IF from transgenic plants was different from human gastric IF. Another difference between IF from human gastric mucosa and IF from transgenic plants is that IF from plants is at the apo-form whereas IF from human beings is a mixture of the apo- and holo-form.

Example 4. TC-Plants

Extracts from one kilogram of transgenic Arabidopsis thaliana (TC-plants) transformed with an extensin-transcobalamin construct (FIG. 5) contained 20 mg of recombinant human TC with CBC. Western blot analysis showed a single band of approximately 45 kDa which reacted with antibodies against human TC (FIG. 11). The calculated molecular weight of mature TC (FIG. 6) with 409 amino acid residues is 45536 Da, showing that the observed and calculated molecular weights are similar. These results show that a plant expression system is able to produce recombinant human TC of the expected size and with CBC.

The transgenic plants were analyzed as described by (16) and shown to contain no cobalamin. This shows that the recombinant human TC was at the apo-form. As for rhIF, rhTC obtained from plants binds to Cbl but not cobinamid (FIG. 12). N-terminal amino acid sequencing showed that the extensin signal peptide was removed from the secreted rhTC generating the normal mature N-terminal found in native human transcobalamin.

Example 5. Purification of the Recombinant Intrinsic Factor from Plants 1 kg of the crude plant material was chopped and homogenized in 2 L of 0.2 M Sodium Phosphate buffer, pH 7.5. The homogenate was centrifuged at 4000 rpm for 10 min and filtered through Watman paper on a Buchner funnel. The filtrate can be stored frozen at that stage. Intrinsic factor was adsorbed from the solution on an affinity matrix according to a previously described method (NexX, E., 1975 Biochim. Biophys. Acta 379, 189-192). After elution from the column intrinsic factor (saturated with cobalamin=holo-form) was subjected to gel filtration, dialyzed against water and lyophilized. Preparation of cobalamin unsaturated intrinsic factor (=apo-form) required an additional step: dialysis against 5 M guanidine HCl for two days followed by dialysis against 0.2 M Sodium Phosphate buffer, pH 7.5.

REFERENCES

1. Allen, R. H. (1975) Prog. Hematol. 9, 57-84.
2. Rothenberg, S. P., and Quadros, E. V. (1995) Bailliere S Clin. Haematol. 8, 499-514.
3. Nicolas, J. P., and Gueant, J. L. (1995) Bailliere S Clin. Haematol. 8, 515-531.
4. Next, E. (1998) in Vitamin B12 and B12-Proteins (Krautler, B., Angoni, D., and Golding, B. T., eds) pp. 461-475, Wiley-VCH, Weinheim, Germany.
5. Hall, C. A., and Begley, J. A. (1977) Am. J. Hum. Genet. 29, 619-626.
6. Katz, M., Mehlman, C. S., and Allen, R. H. (1974) J. Clin. Invest. 53, 1274-1283.
7. Li, N., Rosenblatt, D. S., Kamen, B. A., Seetharam, S., and Seetharam, B. (1994) Hum, Mol, Genet. 3, 1835-1840.
8. VanKapel, J., Loef, B. G., Lindemans, J., and Abels, J. (1981) Biochim, Biophys. Acta 676, 307-313.
9. Quadros, E. V., Rothenberg, S. P., Pan, Y. C., and Stein, S. (1986) J. Biol. Chem. 261, 15455-15460.
10. Gordon, M., Chokshi, H., and Alpers, D. H. (1992) Biochim. Biophys. Acta 1132, 276-283.
11. Quadros, E. V., Sai, P., and Rothenberg, S. P. (1993) Blood 81, 1239-1245.
12. Fedosov, S. N., Berglund, L., Next, E., and Petersen, T. E. (1999) J. Biol. Chem. 274, 26015-26020.
13. Wen, J., Kinnear, M. B., Richardson, M. A., Willetts, N. S., Russell-Jones, G. J., Gordon, M. M., and Alpers, D. H. (2000) Biochim. Biophys. Acta 1490, 43-53.
14. Next, E. and Andersen, J. (1977) Scand. J. Clin. Lab. Invest. 37, 723-728.
15. Stupperich, E. And Next, E. (1991) Eur. J. Biochem. 199, 299-303.
16. Next, E. And Gimsing, P. (1981) Scand. J. Clin. Lab. Invest. 41, 465-468.
17. Clough, S. J., and Bent, A. F. (1998) Plant J. 16, 735-743.
18. Koncz, C., and Schell, J. (1986) Mol. Gen. Genet. 204, 383-396.
19. Nexo et al. 2000, Clinical Chemistry 46 (10): 1643-1649
20 Next, 1975, Biochim. Biophys. Acta, 379: 189-192.

The invention claimed is:

1. A composition, the composition comprising intrinsic factor and a plant specific carbohydrate chain on the intrinsic factor, wherein all of the intrinsic factor is in the apo form.

* * * * *

SEQUENCE LISTING

<160> NUMBER OF SEQ ID NOS: 13

<210> SEQ ID NO 1
<211> LENGTH: 22
<212> TYPE: PRT
<213> ORGANISM: Arabidopsis thaliana

<400> SEQUENCE: 1

Met Ala Ser Ser Ser Ile Ala Leu Phe Leu Ala Leu Asn Leu Leu Phe
1               5                   10                  15

Phe Thr Thr Ile Ser Ala
            20

<210> SEQ ID NO 2
<211> LENGTH: 1430
<212> TYPE: DNA
<213> ORGANISM: Artificial Sequence
<220> FEATURE:
<223> OTHER INFORMATION: extensin-IF fusion protein
<220> FEATURE:
<221> NAME/KEY: CDS
<222> LOCATION: (54)..(1316)
<223> OTHER INFORMATION: extensin-IF fusion protein

<400> SEQUENCE: 2

```
tctagaactc acaacctagc tagctagtaa acagtatttt ctatatacca aaa atg         56
                                                          Met
                                                          1 gct tca agt tcc ata gct ctt ttc ttg gct ctc aat ctt ctc ttt ttc       104
Ala Ser Ser Ser Ile Ala Leu Phe Leu Ala Leu Asn Leu Leu Phe Phe
        5                   10                  15 aca aca atc tcc gcc agt acc cag acc cag agt tca tgc tcc gtt ccc       152
Thr Thr Ile Ser Ala Ser Thr Gln Thr Gln Ser Ser Cys Ser Val Pro
            20                  25                  30 tca gca cag gag ccc ttg gtc aat gga ata caa gta ctc atg gag aac       200
Ser Ala Gln Glu Pro Leu Val Asn Gly Ile Gln Val Leu Met Glu Asn
    35                  40                  45 tcg gtg act tca tca gcc tac cca aac ccc agc atc ctg att gcc atg       248
Ser Val Thr Ser Ser Ala Tyr Pro Asn Pro Ser Ile Leu Ile Ala Met
50                  55                  60                  65 aat ctg gcc gga gcc tac aac ttg aag gcc cag aag ctc ctg act tac       296
Asn Leu Ala Gly Ala Tyr Asn Leu Lys Ala Gln Lys Leu Leu Thr Tyr
                70                  75                  80 cag ctc atg tcc agc gac aac aac gat cta acc att ggg cag ctc ggc       344
Gln Leu Met Ser Ser Asp Asn Asn Asp Leu Thr Ile Gly Gln Leu Gly
            85                  90                  95 ctc acc atc atg gcc ctc acc tcc tcc tgc cga gac cct ggg gat aaa       392
Leu Thr Ile Met Ala Leu Thr Ser Ser Cys Arg Asp Pro Gly Asp Lys
        100                 105                 110 gta tcc att cta caa aga caa atg gag aac tgg gca cct tcc agc ccc       440
Val Ser Ile Leu Gln Arg Gln Met Glu Asn Trp Ala Pro Ser Ser Pro
    115                 120                 125 aac gct gaa gca tca gcc ttc tat ggg ccc agt cta gcg atc ttg gca       488
Asn Ala Glu Ala Ser Ala Phe Tyr Gly Pro Ser Leu Ala Ile Leu Ala
130                 135                 140                 145 ctg tgc cag aag aac tct gag gcg acc ttg ccg ata gcc gtc cgc ttt       536
Leu Cys Gln Lys Asn Ser Glu Ala Thr Leu Pro Ile Ala Val Arg Phe
                150                 155                 160 gcc aag acc ctg ctg gcc aac tcc tct ccc ttc aat gta gac aca gga       584
Ala Lys Thr Leu Leu Ala Asn Ser Ser Pro Phe Asn Val Asp Thr Gly
            165                 170                 175 gca atg gca acc ttg gct ctg acc tgt atg tac aac aag atc cct gta       632
```

```
                Ala Met Ala Thr Leu Ala Leu Thr Cys Met Tyr Asn Lys Ile Pro Val
                            180                 185                 190 ggt tca gag gaa ggt tac aga tcc ctg ttt ggt cag gta cta aag gat        680
Gly Ser Glu Glu Gly Tyr Arg Ser Leu Phe Gly Gln Val Leu Lys Asp
        195                 200                 205 att gtg gag aaa atc agc atg aag atc aaa gat aat ggc atc att gga        728
Ile Val Glu Lys Ile Ser Met Lys Ile Lys Asp Asn Gly Ile Ile Gly
210                 215                 220                 225 gac atc tac agt act ggc ctc gcc atg cag gct ctc tct gta aca cct        776
Asp Ile Tyr Ser Thr Gly Leu Ala Met Gln Ala Leu Ser Val Thr Pro
                230                 235                 240 gag cca tct aaa aag gaa tgg aac tgc aag aag act acg gat atg ata        824
Glu Pro Ser Lys Lys Glu Trp Asn Cys Lys Lys Thr Thr Asp Met Ile
            245                 250                 255 ctc aat gag att aag cag ggg aaa ttc cac aac ccc atg tcc att gct        872
Leu Asn Glu Ile Lys Gln Gly Lys Phe His Asn Pro Met Ser Ile Ala
        260                 265                 270 caa atc ctc cct tcc ctg aaa ggc aag aca tac cta gat gtg ccc cag        920
Gln Ile Leu Pro Ser Leu Lys Gly Lys Thr Tyr Leu Asp Val Pro Gln
275                 280                 285 gtc act tgt agt cct gat cat gag gta caa cca act cta ccc agc aac        968
Val Thr Cys Ser Pro Asp His Glu Val Gln Pro Thr Leu Pro Ser Asn
290                 295                 300                 305 cct ggc cct ggc ccc acc tct gca tct aac atc act gtc ata tac acc       1016
Pro Gly Pro Gly Pro Thr Ser Ala Ser Asn Ile Thr Val Ile Tyr Thr
                310                 315                 320 ata aat aac cag ctg agg ggg gtt gag ctg ctc ttc aac gag acc atc       1064
Ile Asn Asn Gln Leu Arg Gly Val Glu Leu Leu Phe Asn Glu Thr Ile
            325                 330                 335 aat gtt agt gtg aaa agt ggg tca gtg tta ctt gtt gtc cta gag gaa       1112
Asn Val Ser Val Lys Ser Gly Ser Val Leu Leu Val Val Leu Glu Glu
        340                 345                 350 gca cag cgc aaa aat cct atg ttc aaa ttt gaa acc aca atg aca tct       1160
Ala Gln Arg Lys Asn Pro Met Phe Lys Phe Glu Thr Thr Met Thr Ser
355                 360                 365 tgg ggc ctt gtc gtc tct tct atc aac aat atc gcg gaa aat gtt aat       1208
Trp Gly Leu Val Val Ser Ser Ile Asn Asn Ile Ala Glu Asn Val Asn
370                 375                 380                 385 cac aag aca tac tgg cag ttt ctt agt ggt gta aca cct ttg aat gaa       1256
His Lys Thr Tyr Trp Gln Phe Leu Ser Gly Val Thr Pro Leu Asn Glu
                390                 395                 400 ggg gtt gct gac tac ata ccc ttc aac cac gag cac atc aca gcc aat       1304
Gly Val Ala Asp Tyr Ile Pro Phe Asn His Glu His Ile Thr Ala Asn
            405                 410                 415 ttc aca cag tac taacgaagag gtgggttcag cttctatcaa acatctccaa           1356
Phe Thr Gln Tyr
        420 aggatgggtg aaatttttc cacttcattt taaatctatg caaaaaagcg aatgcctgtg      1416 atgctacccc cggg                                                       1430

<210> SEQ ID NO 3
<211> LENGTH: 421
<212> TYPE: PRT
<213> ORGANISM: Artificial Sequence
<220> FEATURE:
<223> OTHER INFORMATION: extensin-IF fusion protein

<400> SEQUENCE: 3

Met Ala Ser Ser Ser Ile Ala Leu Phe Leu Ala Leu Asn Leu Leu Phe
1               5                   10                  15
```

```
Phe Thr Thr Ile Ser Ala Ser Thr Gln Thr Gln Ser Ser Cys Ser Val
                20                  25                  30

Pro Ser Ala Gln Glu Pro Leu Val Asn Gly Ile Gln Val Leu Met Glu
        35                  40                  45

Asn Ser Val Thr Ser Ser Ala Tyr Pro Asn Pro Ser Ile Leu Ile Ala
 50                  55                  60

Met Asn Leu Ala Gly Ala Tyr Asn Leu Lys Ala Gln Lys Leu Leu Thr
 65                  70                  75                  80

Tyr Gln Leu Met Ser Ser Asp Asn Asp Leu Thr Ile Gly Gln Leu
                85                  90                  95

Gly Leu Thr Ile Met Ala Leu Thr Ser Ser Cys Arg Asp Pro Gly Asp
            100                 105                 110

Lys Val Ser Ile Leu Gln Arg Gln Met Glu Asn Trp Ala Pro Ser Ser
            115                 120                 125

Pro Asn Ala Glu Ala Ser Ala Phe Tyr Gly Pro Ser Leu Ala Ile Leu
    130                 135                 140

Ala Leu Cys Gln Lys Asn Ser Glu Ala Thr Leu Pro Ile Ala Val Arg
145                 150                 155                 160

Phe Ala Lys Thr Leu Leu Ala Asn Ser Ser Pro Phe Asn Val Asp Thr
                165                 170                 175

Gly Ala Met Ala Thr Leu Ala Leu Thr Cys Met Tyr Asn Lys Ile Pro
            180                 185                 190

Val Gly Ser Glu Glu Gly Tyr Arg Ser Leu Phe Gly Gln Val Leu Lys
            195                 200                 205

Asp Ile Val Glu Lys Ile Ser Met Lys Ile Lys Asp Asn Gly Ile Ile
    210                 215                 220

Gly Asp Ile Tyr Ser Thr Gly Leu Ala Met Gln Ala Leu Ser Val Thr
225                 230                 235                 240

Pro Glu Pro Ser Lys Lys Glu Trp Asn Cys Lys Lys Thr Thr Asp Met
                245                 250                 255

Ile Leu Asn Glu Ile Lys Gln Gly Lys Phe His Asn Pro Met Ser Ile
            260                 265                 270

Ala Gln Ile Leu Pro Ser Leu Lys Gly Lys Thr Tyr Leu Asp Val Pro
            275                 280                 285

Gln Val Thr Cys Ser Pro Asp His Glu Val Gln Pro Thr Leu Pro Ser
    290                 295                 300

Asn Pro Gly Pro Gly Pro Thr Ser Ala Ser Asn Ile Thr Val Ile Tyr
305                 310                 315                 320

Thr Ile Asn Asn Gln Leu Arg Gly Val Glu Leu Leu Phe Asn Glu Thr
                325                 330                 335

Ile Asn Val Ser Val Lys Ser Gly Ser Val Leu Leu Val Leu Glu
            340                 345                 350

Glu Ala Gln Arg Lys Asn Pro Met Phe Lys Phe Glu Thr Thr Met Thr
            355                 360                 365

Ser Trp Gly Leu Val Val Ser Ser Ile Asn Asn Ile Ala Glu Asn Val
    370                 375                 380

Asn His Lys Thr Tyr Trp Gln Phe Leu Ser Gly Val Thr Pro Leu Asn
385                 390                 395                 400

Glu Gly Val Ala Asp Tyr Ile Pro Phe Asn His Glu His Ile Thr Ala
                405                 410                 415

Asn Phe Thr Gln Tyr
            420
```

<210> SEQ ID NO 4
<211> LENGTH: 399
<212> TYPE: PRT
<213> ORGANISM: homo sapiens

<400> SEQUENCE: 4

```
Ser Thr Gln Thr Gln Ser Ser Cys Ser Val Pro Ser Ala Gln Glu Pro
1               5                   10                  15

Leu Val Asn Gly Ile Gln Val Leu Met Glu Asn Ser Val Thr Ser Ser
            20                  25                  30

Ala Tyr Pro Asn Pro Ser Ile Leu Ile Ala Met Asn Leu Ala Gly Ala
        35                  40                  45

Tyr Asn Leu Lys Ala Gln Lys Leu Leu Thr Tyr Gln Leu Met Ser Ser
    50                  55                  60

Asp Asn Asn Asp Leu Thr Ile Gly Gln Leu Gly Leu Thr Ile Met Ala
65                  70                  75                  80

Leu Thr Ser Ser Cys Arg Asp Pro Gly Asp Lys Val Ser Ile Leu Gln
                85                  90                  95

Arg Gln Met Glu Asn Trp Ala Pro Ser Ser Pro Asn Ala Glu Ala Ser
            100                 105                 110

Ala Phe Tyr Gly Pro Ser Leu Ala Ile Leu Ala Leu Cys Gln Lys Asn
        115                 120                 125

Ser Glu Ala Thr Leu Pro Ile Ala Val Arg Phe Ala Lys Thr Leu Leu
    130                 135                 140

Ala Asn Ser Ser Pro Phe Asn Val Asp Thr Gly Ala Met Ala Thr Leu
145                 150                 155                 160

Ala Leu Thr Cys Met Tyr Asn Lys Ile Pro Val Gly Ser Glu Glu Gly
                165                 170                 175

Tyr Arg Ser Leu Phe Gly Gln Val Leu Lys Asp Ile Val Glu Lys Ile
            180                 185                 190

Ser Met Lys Ile Lys Asp Asn Gly Ile Ile Gly Asp Ile Tyr Ser Thr
        195                 200                 205

Gly Leu Ala Met Gln Ala Leu Ser Val Thr Pro Glu Pro Ser Lys Lys
    210                 215                 220

Glu Trp Asn Cys Lys Lys Thr Thr Asp Met Ile Leu Asn Glu Ile Lys
225                 230                 235                 240

Gln Gly Lys Phe His Asn Pro Met Ser Ile Ala Gln Ile Leu Pro Ser
                245                 250                 255

Leu Lys Gly Lys Thr Tyr Leu Asp Val Pro Gln Val Thr Cys Ser Pro
            260                 265                 270

Asp His Glu Val Gln Pro Thr Leu Pro Ser Asn Pro Gly Pro Gly Pro
        275                 280                 285

Thr Ser Ala Ser Asn Ile Thr Val Ile Tyr Thr Ile Asn Asn Gln Leu
    290                 295                 300

Arg Gly Val Glu Leu Leu Phe Asn Glu Thr Ile Asn Val Ser Val Lys
305                 310                 315                 320

Ser Gly Ser Val Leu Leu Val Leu Glu Glu Ala Gln Arg Lys Asn
                325                 330                 335

Pro Met Phe Lys Phe Glu Thr Thr Met Thr Ser Trp Gly Leu Val Val
            340                 345                 350

Ser Ser Ile Asn Asn Ile Ala Glu Asn Val Asn His Lys Thr Tyr Trp
        355                 360                 365

Gln Phe Leu Ser Gly Val Thr Pro Leu Asn Glu Gly Val Ala Asp Tyr
    370                 375                 380
```

```
Ile Pro Phe Asn His Glu His Ile Thr Ala Asn Phe Thr Gln Tyr
385                 390                 395

<210> SEQ ID NO 5
<211> LENGTH: 129
<212> TYPE: DNA
<213> ORGANISM: Phaseolus vulgaris
<220> FEATURE:
<221> NAME/KEY: CDS
<222> LOCATION: (52)..(129)

<400> SEQUENCE: 5
tctagaagag agggaaggaa gggaaacgga aagagagaaa gagaaagaga a atg aag      57
                                                        Met Lys
                                                        1 aag aat agg atg atg att atg ata tgc agt gta gga gtg gtg tgg atg     105
Lys Asn Arg Met Met Ile Met Ile Cys Ser Val Gly Val Val Trp Met
        5                   10                  15 ctg tta gtt gga gga agc tac gga                                     129
Leu Leu Val Gly Gly Ser Tyr Gly
    20                  25

<210> SEQ ID NO 6
<211> LENGTH: 26
<212> TYPE: PRT
<213> ORGANISM: Phaseolus vulgaris

<400> SEQUENCE: 6

Met Lys Lys Asn Arg Met Met Ile Met Ile Cys Ser Val Gly Val Val
1               5                   10                  15

Trp Met Leu Leu Val Gly Gly Ser Tyr Gly
            20                  25

<210> SEQ ID NO 7
<211> LENGTH: 144
<212> TYPE: DNA
<213> ORGANISM: Nicotiana tabacum
<220> FEATURE:
<221> NAME/KEY: CDS
<222> LOCATION: (49)..(144)

<400> SEQUENCE: 7
tctagaagct cgttgttcat cttaattctc ccaacaagtc ttcccatc atg tct acc     57
                                                    Met Ser Thr
                                                    1 tca cat aaa cat aat act cct caa atg gct gct atc aca ctc cta gga    105
Ser His Lys His Asn Thr Pro Gln Met Ala Ala Ile Thr Leu Leu Gly
        5                   10                  15 tta cta ctt gtt gcc agc agc att gac ata gca ggg gct                144
Leu Leu Leu Val Ala Ser Ser Ile Asp Ile Ala Gly Ala
    20                  25                  30

<210> SEQ ID NO 8
<211> LENGTH: 32
<212> TYPE: PRT
<213> ORGANISM: Nicotiana tabacum

<400> SEQUENCE: 8

Met Ser Thr Ser His Lys His Asn Thr Pro Gln Met Ala Ala Ile Thr
1               5                   10                  15

Leu Leu Gly Leu Leu Leu Val Ala Ser Ser Ile Asp Ile Ala Gly Ala
            20                  25                  30
```

```
<210> SEQ ID NO 9
<211> LENGTH: 1355
<212> TYPE: DNA
<213> ORGANISM: Artificial Sequence
<220> FEATURE:
<223> OTHER INFORMATION: extensin-transcobalamin fusion protein
<220> FEATURE:
<221> NAME/KEY: CDS
<222> LOCATION: (54)..(1346)
<223> OTHER INFORMATION: extensin-transcobalamin fusion protein

<400> SEQUENCE: 9
```

| | | | | | | | | | | | | | | | | |
|---|---|---|---|---|---|---|---|---|---|---|---|---|---|---|---|---|
| tctagaactc | acaacctagc | tagctagtaa | acagtattt | ctatatacca | aaa | atg | | | | | | | | | | 56 |
| | | | | | | Met | | | | | | | | | | |
| | | | | | | 1 | | | | | | | | | | |

| gct | tca | agt | tcc | ata | gct | ctt | ttc | ttg | gct | ctc | aat | ctt | ctc | ttt | ttc | 104 |
|---|---|---|---|---|---|---|---|---|---|---|---|---|---|---|---|---|
| Ala | Ser | Ser | Ser | Ile | Ala | Leu | Phe | Leu | Ala | Leu | Asn | Leu | Leu | Phe | Phe | |
| | | | 5 | | | | 10 | | | | | 15 | | | | |

| aca | aca | atc | tcc | gcc | gag | atg | tgt | gaa | ata | cca | gag | atg | gac | agc | cat | 152 |
|---|---|---|---|---|---|---|---|---|---|---|---|---|---|---|---|---|
| Thr | Thr | Ile | Ser | Ala | Glu | Met | Cys | Glu | Ile | Pro | Glu | Met | Asp | Ser | His | |
| | | 20 | | | | | 25 | | | | 30 | | | | | |

| ctg | gta | gag | aag | ttg | ggc | cag | cac | ctc | tta | cct | tgg | atg | gac | cgg | ctt | 200 |
|---|---|---|---|---|---|---|---|---|---|---|---|---|---|---|---|---|
| Leu | Val | Glu | Lys | Leu | Gly | Gln | His | Leu | Leu | Pro | Trp | Met | Asp | Arg | Leu | |
| | 35 | | | | | 40 | | | | | 45 | | | | | |

| tcc | ctg | gag | cac | ttg | aac | ccc | agc | atc | tat | gtg | ggc | cta | cgc | ctc | tcc | 248 |
|---|---|---|---|---|---|---|---|---|---|---|---|---|---|---|---|---|
| Ser | Leu | Glu | His | Leu | Asn | Pro | Ser | Ile | Tyr | Val | Gly | Leu | Arg | Leu | Ser | |
| 50 | | | | | 55 | | | | | 60 | | | | | 65 | |

| agt | ctg | cag | gct | ggg | acc | aag | gaa | gac | ctc | tac | ctg | cac | agc | ctc | aag | 296 |
|---|---|---|---|---|---|---|---|---|---|---|---|---|---|---|---|---|
| Ser | Leu | Gln | Ala | Gly | Thr | Lys | Glu | Asp | Leu | Tyr | Leu | His | Ser | Leu | Lys | |
| | | | | 70 | | | | | 75 | | | | | 80 | | |

| ctt | ggt | tac | cag | cag | tgc | ctc | cta | ggg | tct | gcc | ttc | agc | gag | gat | gac | 344 |
|---|---|---|---|---|---|---|---|---|---|---|---|---|---|---|---|---|
| Leu | Gly | Tyr | Gln | Gln | Cys | Leu | Leu | Gly | Ser | Ala | Phe | Ser | Glu | Asp | Asp | |
| | | | 85 | | | | | 90 | | | | | 95 | | | |

| ggt | gac | tgc | cag | ggc | aag | cct | tcc | atg | ggc | cag | ctg | gcc | ctc | tac | ctg | 392 |
|---|---|---|---|---|---|---|---|---|---|---|---|---|---|---|---|---|
| Gly | Asp | Cys | Gln | Gly | Lys | Pro | Ser | Met | Gly | Gln | Leu | Ala | Leu | Tyr | Leu | |
| | | 100 | | | | | 105 | | | | | 110 | | | | |

| ctc | gct | ctc | aga | gcc | aac | tgt | gag | ttt | gtc | agg | ggc | cac | aag | ggg | gac | 440 |
|---|---|---|---|---|---|---|---|---|---|---|---|---|---|---|---|---|
| Leu | Ala | Leu | Arg | Ala | Asn | Cys | Glu | Phe | Val | Arg | Gly | His | Lys | Gly | Asp | |
| | 115 | | | | | 120 | | | | | 125 | | | | | |

| agg | ctg | gtc | tca | cag | ctc | aaa | tgg | ttc | ctg | gag | gat | gag | aag | aga | gcc | 488 |
|---|---|---|---|---|---|---|---|---|---|---|---|---|---|---|---|---|
| Arg | Leu | Val | Ser | Gln | Leu | Lys | Trp | Phe | Leu | Glu | Asp | Glu | Lys | Arg | Ala | |
| 130 | | | | | 135 | | | | | 140 | | | | | 145 | |

| att | ggg | cat | gat | cac | aag | ggc | cac | ccc | cac | act | agc | tac | tac | cag | tat | 536 |
|---|---|---|---|---|---|---|---|---|---|---|---|---|---|---|---|---|
| Ile | Gly | His | Asp | His | Lys | Gly | His | Pro | His | Thr | Ser | Tyr | Tyr | Gln | Tyr | |
| | | | | 150 | | | | | 155 | | | | | 160 | | |

| ggc | ctg | ggc | att | ctg | gcc | ctg | tgt | ctc | cac | cag | aag | cgg | gtc | cat | gac | 584 |
|---|---|---|---|---|---|---|---|---|---|---|---|---|---|---|---|---|
| Gly | Leu | Gly | Ile | Leu | Ala | Leu | Cys | Leu | His | Gln | Lys | Arg | Val | His | Asp | |
| | | | 165 | | | | | 170 | | | | | 175 | | | |

| agc | gtg | gtg | gac | aaa | ctt | ctg | tat | gct | gtg | gaa | cct | ttc | cac | cag | ggc | 632 |
|---|---|---|---|---|---|---|---|---|---|---|---|---|---|---|---|---|
| Ser | Val | Val | Asp | Lys | Leu | Leu | Tyr | Ala | Val | Glu | Pro | Phe | His | Gln | Gly | |
| | | 180 | | | | | 185 | | | | | 190 | | | | |

| cac | cat | tct | gtg | gac | aca | gca | gcc | atg | gca | ggc | ttg | gca | ttc | acc | tgt | 680 |
|---|---|---|---|---|---|---|---|---|---|---|---|---|---|---|---|---|
| His | His | Ser | Val | Asp | Thr | Ala | Ala | Met | Ala | Gly | Leu | Ala | Phe | Thr | Cys | |
| | 195 | | | | | 200 | | | | | 205 | | | | | |

| ctg | aag | cgc | tca | aac | ttc | aac | cct | ggt | cgg | aga | caa | cgg | atc | acc | atg | 728 |
|---|---|---|---|---|---|---|---|---|---|---|---|---|---|---|---|---|
| Leu | Lys | Arg | Ser | Asn | Phe | Asn | Pro | Gly | Arg | Arg | Gln | Arg | Ile | Thr | Met | |
| 210 | | | | | 215 | | | | | 220 | | | | | 225 | |

| gcc | atc | aga | aca | gtg | cga | gag | gag | atc | ttg | aag | gcc | cag | acc | ccc | gag | 776 |
|---|---|---|---|---|---|---|---|---|---|---|---|---|---|---|---|---|
| Ala | Ile | Arg | Thr | Val | Arg | Glu | Glu | Ile | Leu | Lys | Ala | Gln | Thr | Pro | Glu | |
| | | | 230 | | | | | 235 | | | | | 240 | | | |

| ggc | cac | ttt | ggg | aat | gtc | tac | agc | acc | cca | ttg | gca | tta | cag | ttc | ctc | 824 |
|---|---|---|---|---|---|---|---|---|---|---|---|---|---|---|---|---|
| Gly | His | Phe | Gly | Asn | Val | Tyr | Ser | Thr | Pro | Leu | Ala | Leu | Gln | Phe | Leu | |

```
            245                 250                 255
atg act tcc ccc atg cct ggg gca gaa ctg gga aca gca tgt ctc aag      872
Met Thr Ser Pro Met Pro Gly Ala Glu Leu Gly Thr Ala Cys Leu Lys
        260                 265                 270 gcg agg gtt gct ttg ctg gcc agt ctg cag gat gga gcc ttc cag aat      920
Ala Arg Val Ala Leu Leu Ala Ser Leu Gln Asp Gly Ala Phe Gln Asn
275                 280                 285 gct ctc atg att tcc cag ctg ctg ccc gtt ctg aac cac aag acc tac      968
Ala Leu Met Ile Ser Gln Leu Leu Pro Val Leu Asn His Lys Thr Tyr
290                 295                 300                 305 att gat ctg atc ttc cca gac tgt ctg gca cca cga gtc atg ttg gaa      1016
Ile Asp Leu Ile Phe Pro Asp Cys Leu Ala Pro Arg Val Met Leu Glu
            310                 315                 320 cca gct gct gag acc att cct cag acc caa gag atc atc agt gtc acg      1064
Pro Ala Ala Glu Thr Ile Pro Gln Thr Gln Glu Ile Ile Ser Val Thr
                325                 330                 335 ctg cag gtg ctt agt ctc ttg ccg ccg tac aga cag tcc atc tct gtt      1112
Leu Gln Val Leu Ser Leu Leu Pro Pro Tyr Arg Gln Ser Ile Ser Val
        340                 345                 350 ctg gcc ggg tcc acc gtg gaa gat gtc ctg aag aag gcc cat gag tta      1160
Leu Ala Gly Ser Thr Val Glu Asp Val Leu Lys Lys Ala His Glu Leu
355                 360                 365 gga gga ttc aca tat gaa aca cag gcc tcc ttg tca ggc ccc tac tta      1208
Gly Gly Phe Thr Tyr Glu Thr Gln Ala Ser Leu Ser Gly Pro Tyr Leu
370                 375                 380                 385 acc tcc gtg atg ggg aaa gcg gcc gga gaa agg gag ttc tgg cag ctt      1256
Thr Ser Val Met Gly Lys Ala Ala Gly Glu Arg Glu Phe Trp Gln Leu
            390                 395                 400 ctc cga gac ccc aac acc cca ctg ttg caa ggt att gct gac tac aga      1304
Leu Arg Asp Pro Asn Thr Pro Leu Leu Gln Gly Ile Ala Asp Tyr Arg
                405                 410                 415 ccc aag gat gga gaa acc att gag ctg agg ctg gtt agc tgg tagcccggg   1355
Pro Lys Asp Gly Glu Thr Ile Glu Leu Arg Leu Val Ser Trp
        420                 425                 430

<210> SEQ ID NO 10
<211> LENGTH: 431
<212> TYPE: PRT
<213> ORGANISM: Artificial Sequence
<220> FEATURE:
<223> OTHER INFORMATION: extensin-transcobalamin fusion protein

<400> SEQUENCE: 10

Met Ala Ser Ser Ile Ala Leu Phe Leu Ala Leu Asn Leu Phe
1               5                   10                  15

Phe Thr Thr Ile Ser Ala Glu Met Cys Glu Ile Pro Glu Met Asp Ser
                20                  25                  30

His Leu Val Glu Lys Leu Gly Gln His Leu Leu Pro Trp Met Asp Arg
            35                  40                  45

Leu Ser Leu Glu His Leu Asn Pro Ser Ile Tyr Val Gly Leu Arg Leu
        50                  55                  60

Ser Ser Leu Gln Ala Gly Thr Lys Glu Asp Leu Tyr Leu His Ser Leu
65                  70                  75                  80

Lys Leu Gly Tyr Gln Gln Cys Leu Leu Gly Ser Ala Phe Ser Glu Asp
                85                  90                  95

Asp Gly Asp Cys Gln Gly Lys Pro Ser Met Gly Gln Leu Ala Leu Tyr
            100                 105                 110

Leu Leu Ala Leu Arg Ala Asn Cys Glu Phe Val Arg Gly His Lys Gly
        115                 120                 125
```

Asp Arg Leu Val Ser Gln Leu Lys Trp Phe Leu Glu Asp Glu Lys Arg
            130                 135                 140

Ala Ile Gly His Asp His Lys Gly His Pro His Thr Ser Tyr Tyr Gln
145                 150                 155                 160

Tyr Gly Leu Gly Ile Leu Ala Leu Cys Leu His Gln Lys Arg Val His
                165                 170                 175

Asp Ser Val Val Asp Lys Leu Leu Tyr Ala Val Glu Pro Phe His Gln
            180                 185                 190

Gly His His Ser Val Asp Thr Ala Ala Met Ala Gly Leu Ala Phe Thr
        195                 200                 205

Cys Leu Lys Arg Ser Asn Phe Asn Pro Gly Arg Gln Arg Ile Thr
    210                 215                 220

Met Ala Ile Arg Thr Val Arg Glu Glu Ile Leu Lys Ala Gln Thr Pro
225                 230                 235                 240

Glu Gly His Phe Gly Asn Val Tyr Ser Thr Pro Leu Ala Leu Gln Phe
                245                 250                 255

Leu Met Thr Ser Pro Met Pro Gly Ala Glu Leu Gly Thr Ala Cys Leu
            260                 265                 270

Lys Ala Arg Val Ala Leu Leu Ala Ser Leu Gln Asp Gly Ala Phe Gln
        275                 280                 285

Asn Ala Leu Met Ile Ser Gln Leu Leu Pro Val Leu Asn His Lys Thr
    290                 295                 300

Tyr Ile Asp Leu Ile Phe Pro Asp Cys Leu Ala Pro Arg Val Met Leu
305                 310                 315                 320

Glu Pro Ala Ala Glu Thr Ile Pro Gln Thr Gln Glu Ile Ile Ser Val
                325                 330                 335

Thr Leu Gln Val Leu Ser Leu Leu Pro Pro Tyr Arg Gln Ser Ile Ser
            340                 345                 350

Val Leu Ala Gly Ser Thr Val Glu Asp Val Leu Lys Lys Ala His Glu
        355                 360                 365

Leu Gly Gly Phe Thr Tyr Glu Thr Gln Ala Ser Leu Ser Gly Pro Tyr
    370                 375                 380

Leu Thr Ser Val Met Gly Lys Ala Ala Gly Glu Arg Glu Phe Trp Gln
385                 390                 395                 400

Leu Leu Arg Asp Pro Asn Thr Pro Leu Leu Gln Gly Ile Ala Asp Tyr
                405                 410                 415

Arg Pro Lys Asp Gly Glu Thr Ile Glu Leu Arg Leu Val Ser Trp
            420                 425                 430

<210> SEQ ID NO 11
<211> LENGTH: 409
<212> TYPE: PRT
<213> ORGANISM: homo sapiens

<400> SEQUENCE: 11

Glu Met Cys Glu Ile Pro Glu Met Asp Ser His Leu Val Glu Lys Leu
1               5                   10                  15

Gly Gln His Leu Leu Pro Trp Met Asp Arg Leu Ser Leu Glu His Leu
            20                  25                  30

Asn Pro Ser Ile Tyr Val Gly Leu Arg Leu Ser Ser Leu Gln Ala Gly
        35                  40                  45

Thr Lys Glu Asp Leu Tyr Leu His Ser Leu Lys Leu Gly Tyr Gln Gln
    50                  55                  60

Cys Leu Leu Gly Ser Ala Phe Ser Glu Asp Asp Gly Asp Cys Gln Gly

```
            65                  70                  75                  80

Lys Pro Ser Met Gly Gln Leu Ala Leu Tyr Leu Leu Ala Leu Arg Ala
                    85                  90                  95

Asn Cys Glu Phe Val Arg Gly His Lys Gly Asp Arg Leu Val Ser Gln
                100                 105                 110

Leu Lys Trp Phe Leu Glu Asp Glu Lys Arg Ala Ile Gly His Asp His
            115                 120                 125

Lys Gly His Pro His Thr Ser Tyr Tyr Gln Tyr Gly Leu Gly Ile Leu
        130                 135                 140

Ala Leu Cys Leu His Gln Lys Arg Val His Asp Ser Val Val Asp Lys
145                 150                 155                 160

Leu Leu Tyr Ala Val Glu Pro Phe His Gln Gly His His Ser Val Asp
                165                 170                 175

Thr Ala Ala Met Ala Gly Leu Ala Phe Thr Cys Leu Lys Arg Ser Asn
                180                 185                 190

Phe Asn Pro Gly Arg Arg Gln Arg Ile Thr Met Ala Ile Arg Thr Val
            195                 200                 205

Arg Glu Glu Ile Leu Lys Ala Gln Thr Pro Glu Gly His Phe Gly Asn
        210                 215                 220

Val Tyr Ser Thr Pro Leu Ala Leu Gln Phe Leu Met Thr Ser Pro Met
225                 230                 235                 240

Pro Gly Ala Glu Leu Gly Thr Ala Cys Leu Lys Ala Arg Val Ala Leu
                245                 250                 255

Leu Ala Ser Leu Gln Asp Gly Ala Phe Gln Asn Ala Leu Met Ile Ser
                260                 265                 270

Gln Leu Leu Pro Val Leu Asn His Lys Thr Tyr Ile Asp Leu Ile Phe
            275                 280                 285

Pro Asp Cys Leu Ala Pro Arg Val Met Leu Glu Pro Ala Ala Glu Thr
        290                 295                 300

Ile Pro Gln Thr Gln Glu Ile Ile Ser Val Thr Leu Gln Val Leu Ser
305                 310                 315                 320

Leu Leu Pro Pro Tyr Arg Gln Ser Ile Ser Val Leu Ala Gly Ser Thr
                325                 330                 335

Val Glu Asp Val Leu Lys Lys Ala His Glu Leu Gly Gly Phe Thr Tyr
                340                 345                 350

Glu Thr Gln Ala Ser Leu Ser Gly Pro Tyr Leu Thr Ser Val Met Gly
            355                 360                 365

Lys Ala Ala Gly Glu Arg Glu Phe Trp Gln Leu Leu Arg Asp Pro Asn
        370                 375                 380

Thr Pro Leu Leu Gln Gly Ile Ala Asp Tyr Arg Pro Lys Asp Gly Glu
385                 390                 395                 400

Thr Ile Glu Leu Arg Leu Val Ser Trp
                405

<210> SEQ ID NO 12
<211> LENGTH: 26
<212> TYPE: PRT
<213> ORGANISM: Phaseolus vulgaris

<400> SEQUENCE: 12

Met Lys Lys Asn Arg Met Met Ile Met Ile Cys Ser Val Gly Val Val
1               5                   10                  15

Trp Met Leu Leu Val Gly Gly Ser Tyr Gly
            20                  25
```

```
<210> SEQ ID NO 13
<211> LENGTH: 32
<212> TYPE: PRT
<213> ORGANISM: Nicotiana tabacum

<400> SEQUENCE: 13

Met Ser Thr Ser His Lys His Asn Thr Pro Gln Met Ala Ala Ile Thr
1               5                   10                  15

Leu Leu Gly Leu Leu Leu Val Ala Ser Ser Ile Asp Ile Ala Gly Ala
            20                  25                  30
```